United States Patent [19]

Uemura et al.

[11] Patent Number: 4,726,835
[45] Date of Patent: Feb. 23, 1988

[54] HERBICIDAL AND PLANT GROWTH REGULATING IMIDAZOLINE DERIVATIVES

[75] Inventors: Masatoshi Uemura; Masashi Sakamoto; Nobuyuki Kikkawa, all of Sodegaura, Japan

[73] Assignee: Idemitsu Kosan Company Limited, Tokyo, Japan

[21] Appl. No.: 934,482

[22] Filed: Nov. 24, 1986

[30] Foreign Application Priority Data

Dec. 2, 1985 [JP] Japan .................. 60-271158
Aug. 7, 1986 [JP] Japan .................. 61-184168

[51] Int. Cl.[4] ............... A01N 43/50; C07D 403/12; C07D 401/12; C07D 413/12
[52] U.S. Cl. ......................... 71/92; 544/109; 544/331; 546/210; 548/301
[58] Field of Search ............. 548/301; 71/92; 546/210; 544/109, 331

[56] References Cited

U.S. PATENT DOCUMENTS 4,122,275 10/1978 Los ........................ 548/301

FOREIGN PATENT DOCUMENTS 5464637 5/1979 Japan .................. 548/301

*Primary Examiner*—Richard A. Schwartz
*Attorney, Agent, or Firm*—Frishauf, Holtz, Goodman & Woodward

[57] ABSTRACT

Imidazoline derivatives represented by the general formula:

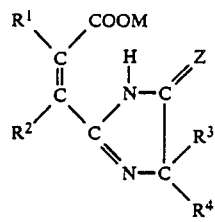

or

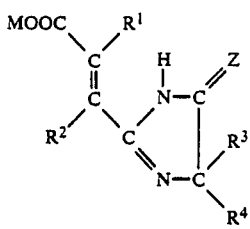

(wherein all the symbols are as defined in appended claims), a process for preparation of said derivatives, and a herbicide or a plant growth regulator containing said derivative as an active component are described. These derivatives are novel compounds, and the herbicide containing said derivative as an active component exhibits excellent herbicidal activity against various weeds without phytotoxicity on useful agricultural products. The plant growth regulator containing said derivatives as an active component exhibits excellent growth regulating activity against turf etc. without phytotoxicity thereon.

16 Claims, No Drawings

HERBICIDAL AND PLANT GROWTH REGULATING IMIDAZOLINE DERIVATIVES

BACKGROUND OF THE INVENTION

The present invention relates to imidazoline derivatives which are novel compounds, a process for preparing them, and a herbicide and a plant growth regulator containing them as an active component.

As disclosed in Japanese Patent Application Laid-Open No. 64637/1979, it is known that imidazolinone derivatives represented by the following general formula have herbicidal activity.

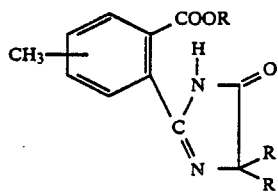

However, the herbicidal activity of the above compounds is not sufficiently high and furthermore the compounds are considered to have problems in that their residual period in the soil is relatively long, they would cause phytotoxicity on succeeding crop or would cause environmental pollution under bad conditions.

In view of the above problems, the present inventors made extensive investigations to develop a herbicide which exhibits high herbicidal activity even when used in a small dose and which has decreased environmental pollution and phytotoxicity on succeeding crop which occurs with persistence in the soil. The compounds also exhibit activity as a plant growth regulator.

In many cases, the herbicidal activity of a chemical substance markedly varies with slight modifications of the structure thereof, specifically in respect of e.g., the type, number and position of groups. Therefore it is difficult to estimate the herbicidal activity of a new compound merely from its similarity in chemical structure to the other compound.

As a result of extensive investigations, it has been found that specified imidazoline derivatives prepared by converting the cyclic structure portion of the benzene ring of the above known imidazoline derivatives into the non-cyclic structure has high herbicidal activity and a high plant growth regulating effect.

SUMMARY OF THE INVENTION

The present invention relates to imidazoline derivatives represented by the general formula (I) or (I'):

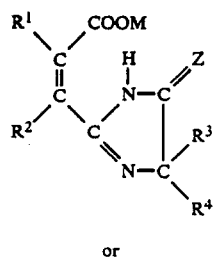

or

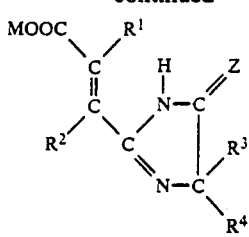

wherein $R^1$ and $R^2$ each represent a hydrogen atom, a lower alkyl group, a cycloalkyl group or a phenyl group, $R^3$ and $R^4$ each represent a lower alkyl group, a cycloalkyl group or a cycloalkyl group in which $R^3$ and $R^4$ are bonded together, Z represents an oxygen atom or a sulfur atom, and M represents a hydrogen atom, a base residue or an ester residue.

The present invention also relates to a process for preparing the imidazoline derivatives of the general formula (I) which comprises the steps of:

reacting maleic anhydride derivatives represented by the general formula:

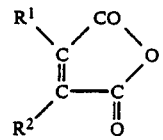

(wherein $R^1$ and $R^2$ are the same as defined above) with amine derivatives represented by the general formula:

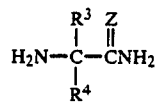

(wherein $R^3$, $R^4$ and Z are the same as defined above) in the presence of a base to form a carbamoylacrylic acid derivative salt represented by the general formula:

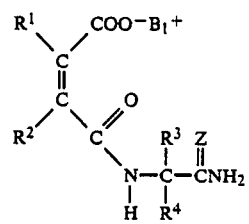

(wherein $R^1$, $R^2$, $R^3$, $R^4$ and Z are the same as defined above, and $B_1$ represents a base residue);

subjecting the above carbamoylacrylic acid derivative salt to a cyclization-dehydration reaction in the presence of a base to form an imidazoline derivative salt represented by the general formula:

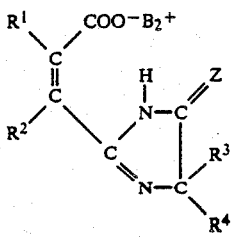

(wherein $R^1$, $R^2$, $R^3$, $R^4$ and Z are the same as defined above, and $B_2$ represents a base residue); and reacting the above imidazoline derivative salt with an acid.

This process is hereinafter referred to as "Process (A)".

The present invention also relates to a process for preparing the imidazoline derivatives of the general formula (I) or (I') which comprises the steps of: reacting an acid halide represented by the general formula:

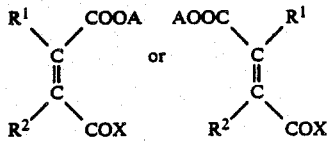

(wherein $R^1$ and $R^2$ are the same as defined above, A represents an ester residue, and X represents a halogen atom) with an amine derivative represented by the general formula:

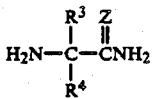

(wherein $R^3$, $R^4$ and Z are the same as defined above) in the presence of a base to form a carbamoylacrylic acid derivative represented by the general formula:

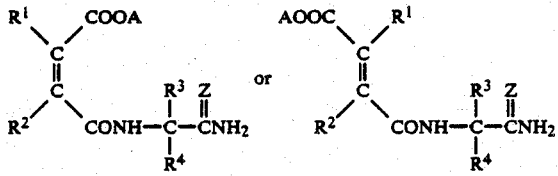

(wherein $R^1$, $R^2$, $R^3$, $R^4$, A and Z are the same as defined above); and
subjecting the above carbamoylacrylic acid derivative to a cyclization-dehydration reaction in the presence of a phosphorus halide.

This process is hereinafter referred to as "Process (B)".

Further, the present invention relates to a herbicide or a plant growth regulator containing the imidazoline derivatives of the general formula (I) or (I') as an active component.

DETAILED DESCRIPTION OF THE INVENTION

The present invention will hereinafter be explained in greater detail.

In the general formula (I) or (I'), $R^1$ and $R^2$ each represent a hydrogen atom, a lower alkyl group having 1 to 4 carbon atoms, such as a methyl group, an ethyl group, a n-propyl group, an isopropyl group and a n-, iso-, sec- or tert-butyl group, a cycloalkyl group having 3 to 6 carbon atoms, such as a cyclopropyl group, a cyclopentyl group and a cyclohexyl group, or a phenyl group.

$R^3$ and $R^4$ each represent the same lower alkyl group as defined in $R^1$ and $R^2$, the same cycloalkyl group as defined in $R^1$ and $R^2$, or a cycloalkyl group in which $R^3$ and $R^4$ are bonded together, such as a cyclopropyl group, a cyclopentyl group and a cyclohexyl group.

Z represents an oxygen atom or a sulfur atom.

M represents a hydrogen atom, a base residue or an ester residue. This base residue includes an alkali metal, an alkaline earth metal and organic ammonium cations. Examples of the alkali metal are sodium (Na), potassium (K), lithium (Li) and rubidium (Rb). Examples of the alkaline earth metal are beryllium (Be), magnesium (Mg), calcium (Ca), strontium (Sr) and barium (Ba). Amines capable of forming organic ammonium cations include methylamine, ethylamine, n-propylamine, isopropylamine, n-butylamine, isobutylamine, sec-butylamine, n-amylamine, iso-amylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, diheptylamine, dioctylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, tauroamine, cyclopentylamine, cyclohexylamine, dicyclohexylamine, piperidine, morpholine and pyrrolidine. In addition, tetraalkylammonium hydroxide such as tetramethylammonium hydroxide, tetraethylammonium hydroxide, trimethylbenzylammonium hydroxide and trimethyl β-hydroxyethyl ammonium hydroxide can be given.

The ester residue represented by M includes an alkyl group having 1 to 12 carbon atoms, such as a methyl group, an ethyl group, a n-propyl group, a n-octyl group, a n-lauryl group, an isopropyl group, an isobutyl group and a tert-butyl group, and also an alkyl group having 1 to 12 carbon atoms, which is substituted with an alkoxyl group having 1 to 3 carbon atoms (e.g., 2-methoxyethyl), a cycloalkyl group having 1 to 6 carbon atoms (e.g., cyclohexyl and (1-cyclopropyl)ethyl), a halogen atom (e.g., 2,2,2-trichloroethyl), a thioalkyl group having 1 to 3 carbon atoms (e.g., methylthiomethyl), a phenyl group (e.g., benzyl, 4-chlorophenethyl, 4-methylphenethyl and 4-methoxyphenethyl), a furyl group (e.g., 2-furylmethyl and 2-tetrahydrofurylmethyl), and so forth. In addition, an alkenyl group having 3 to 5 carbon atoms, such as allyl, 1,1-dimethylallyl and 2-methylallyl, a halogen-substituted alkenyl group such as 2-chloroallyl and 2,3-dichloroallyl, and a phenyl-substituted alkenyl group such as 3-phenylallyl, 3-(4-chlorophenyl)allyl, 3-(4-methylphenyl)allyl and 3-(4-methoxyphenyl)allyl can be given. In addition, an alkynyl group having 3 to 5 carbon atoms, such as propargyl, 1-methylpropargyl, 1,1-dimethylpropargyl and 3-methylpropargyl, a phenyl-substituted alkynyl group such as 3-phenylpropargyl, a hydroxyl group-containing alkynyl group such as 3-hydroxymethylpropargyl, and a substituted phenyl group such as 4-chlorophenyl, 4-methylphenyl and 4-methoxyphenyl can be given.

$B_1$ and $B_2$ each represent a base residue among M. More specifically, $B_1$ and $B_2$ each represent an alkali metal, an alkaline earth metal, or an organic ammonium cation.

Representative examples of the imidazoline derivatives of the general formula (I) or (I') other than the derivatives prepared in Preparation Examples hereinafter are 3-methyl- 3-Z-(4-cyclohexyl-4-methyl-5-oxo-2-imidazoline-2-yl)acrylic acid, sodium 2-(methyl-3-Z-(4-ethyl-4-isopropyl-5-oxo-2-imidazoline-2-yl)acrylate, potassium 2-ethyl-3-propyl-3-Z-(4-butyl-4-propyl-5-oxo-2-imidazoline-2-yl)acrylate, calcium 2-propyl-3-ethyl-3-Z-(4,4-pentamethylene-5-oxo-2-imidazoline-2-yl)acrylate, magnesium 2-isopropyl-3-butyl-3-Z-(4-isopropyl-4-methyl-5-oxo-2-imidazoline-2-yl)acrylate, triethylammonium 2-butyl-3-isopropyl-3-Z-(4-isopropyl-4-methyl-5-oxo-2-imidazoline-2-yl)acrylate, diethylammonium 2-cyclohexyl-3-methyl-3-Z-(4-isopropyl-4-methyl-5-oxo-2-imidazoline-2-yl)acrylate, isopropylammonium 2-methyl-3-cyclohexyl-3-Z-(4-isopropyl-4-methyl-5-oxo-2-imidazoline-2-yl)acrylate, 2-methylallylammonium 3-methyl-3-Z-(4-cyclohexyl-4-methyl-5-oxo-2-imidazoline-2-yl)acrylate, propargylammonium 2-methyl-3-Z-(4-ethyl-4-isopropyl-5-oxo-2-imidazoline-2-yl)acrylate, di-2-ethanolammonium 2-ethyl-3-propyl-3-Z-(4-butyl-4-propyl-5-oxo-2-imidazoline-2-yl)acrylate, 2-ethoxyethylammonium 2-propyl-3-ethyl-3-Z-(4,4-pentamethylene-5-oxo-2-imidazoline-2-yl)acrylate, cyclohexylammonium 2-isopropyl-3-butyl-3-Z-(4-isopropyl-4-methyl-5-oxo-2-imidazoline-2-yl)acrylate, piperidinium 2-butyl-3-isopropyl-3-Z-(4-isopropyl-4-methyl-5-oxo-2-imidazoline-2-yl)acrylate, morpholium 2-cyclohexyl-3-methyl-3-Z-(4-isopropyl-4-methyl-5-oxo-2-imidazoline-2-yl)acrylate, pyrrolidinium 2-methyl-3-cyclohexyl-3-Z-(4-isopropyl-4-methyl-5-oxo-2-imidazoline-2-yl)acrylate, benzyltriethylammonium 3-methyl-3-Z-(4-cyclohexyl-4-methyl-5-oxo-2-imidazoline-2-yl)acrylate, methyl 2-methyl-3-Z-(4-ethyl-4-isopropyl-5-oxo-2-imidazoline-2-yl)acrylate, ethyl 2-ethyl-3-propyl-3-Z-(4-butyl-4-propyl-5-oxo-2-imidazoline-2-yl)acrylate, propyl 2-propyl-3-ethyl-3-Z-(4,4-pentamethylene-5-oxo-2-imidazoline-2-yl)acrylate, octyl 2-isopropyl-3-butyl-3-Z-(4-isopropyl-4-methyl-5-oxo-2-imidazoline-2-yl)acrylate, laury 2-butyl-3-isopropyl-3-Z-(4-isopropyl-4-methyl-5-oxo-2-imidazoline-2-yl)acrylate, isopropyl 2-cyclohexyl-3-methyl-3-Z-(4-isopropyl-4-methyl-5-oxo-2-imidazoline-2-yl)acrylate, isobutyl 2-methyl-3-cyclohexyl-3-Z-(4-isopropyl-4-methyl-5-oxo-2-imidazoline-2-yl)acrylate, tert-butyl 3-methyl-3-Z-(4-cyclohexyl-4-methyl-5-oxo-2-imidazoline-2-yl)acrylate, 2-methoxyethyl 2-methyl-3-Z-(4-ethyl-4-isopropyl-5-oxo-2-imidazoline-2-yl)acrylate, cyclohexyl 2-ethyl-3-propyl-3-Z-(4-butyl-4-propyl-5-oxo-2-imidazoline-2-yl)acrylate, (1-cyclopropyl)ethyl 2-propyl-3-ethyl-3-Z-(4,4-pentamethylene-5-oxo-2-imidazoline-2-yl)acrylate, 2,2,2-trichloroethyl 2-isopropyl-3-butyl-3-Z-(4-isopropyl-4-methyl-5-oxo-2-imidazoline-2-yl)acrylate, methylthiomethyl 2-butyl-3-isopropyl-3-Z-(4-isopropyl-4-methyl-5-oxo-2-imidazoline-2-yl)acrylate, benzyl 2-cyclohexyl-3-methyl-3-Z-(4-isopropyl-4-methyl-5-oxo-2-imidazoline-2-yl)acrylate, phenetyl 2-methyl-3-cyclohexyl-3-Z-(4-isopropyl-4-methyl-5-oxo-2-imidazoline-2-yl)acrylate, (2-furyl)methyl 2-sec-butyl-3-isobutyl-3-Z-(4-sec-butyl-4-methyl-5-oxo-2-imidazoline-2-yl)acrylate, (2-tetrahydrofuryl)methyl 2-isobutyl-3-sec-butyl-3-Z-(4-isobutyl-4-methyl-5-oxo-2-imidazoline-2-yl)acrylate, 1,1-dimethylallyl 2-sec-butyl-3-isobutyl-3-Z-(4-sec-butyl-4-methyl-5-oxo-2-imidazoline-2-yl)acrylate, 2-chloroallyl 2-isobutyl-3-sec-butyl-3-Z-(4-isobutyl-4-methyl-5-oxo-2-imidazoline-2-yl)acrylate, 3-(p-tolyl)allyl 2-sec-butyl-3-isobutyl-3-Z-(4-sec-butyl-4-methyl-5-oxo-2-imidazoline-2-yl)acrylate, 3-(p-anisyl)allyl 2-isobutyl-3-sec-butyl-3-Z-(4-isobutyl-4-methyl-5-oxo-2-imidazoline-2-yl)acrylate, 1,1-dimethylpropargyl 2-sec-butyl-3-isobutyl-3-Z-(4-sec-butyl-4-methyl-5-oxo-2-imidazoline-2-yl)acrylate, 3-phenylpropargyl 2-isobutyl-3-sec-butyl-3-Z-(4-isobutyl-4-methyl-5-oxo-2-imidazoline-2-yl)acrylate, p-tolyl 2-sec-butyl-3-isobutyl-3-Z-(4-sec-butyl-4-methyl-5-oxo-2-imidazoline-2-yl)acrylate, anisyl 2-isobutyl-3-sec-butyl-3-Z-(4-isobutyl-4-methyl-5-oxo-2-imidazoline-2-yl)acrylate, 2-methyl-3-phenyl-3-Z-(4-isopropyl-4-methyl-5-oxo-2-imidazoline-2-yl)acrylic acid, 2,3-dimethyl-3-E-(4-isopropyl-4-methyl-5-oxo-2-imidazoline-2-yl)acrylic acid, sodium-2,3-dimethyl-3-Z-(4-isopropyl-4-methyl-5-thiono-2-imidazoline-2-yl)acrylate, isopropyl ammonium-2,3-dimethyl-3-Z-(4-isopropyl-4-methyl-5-thiono-2-imidazoline-2-yl)acrylate, 2,3-dimethyl-3-Z-(4-ethyl-4-methyl-5-thiono-2-imidazoline-2-yl)acrylic acid, 2-phenyl-3-methyl-3-Z-(4-isopropyl-4-methyl-5-thiono-2-imidazoline-2-yl)acrylic acid, and 2-methyl-3-ethyl-3-Z-(4-isopropyl-4-methyl-5-thiono-2-imidazoline-2-yl)acrylic acid.

The imidazoline derivatives of the general formula (I) or (I') of the present invention can be prepared by various processes. Of these processes, Process A and Process B can be given as efficient processes.

Process A

In accordance with Process A, the reaction is carried out according to the following sequence:

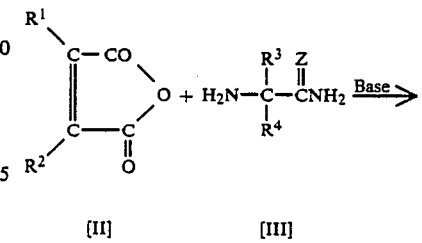

[II]     [III]

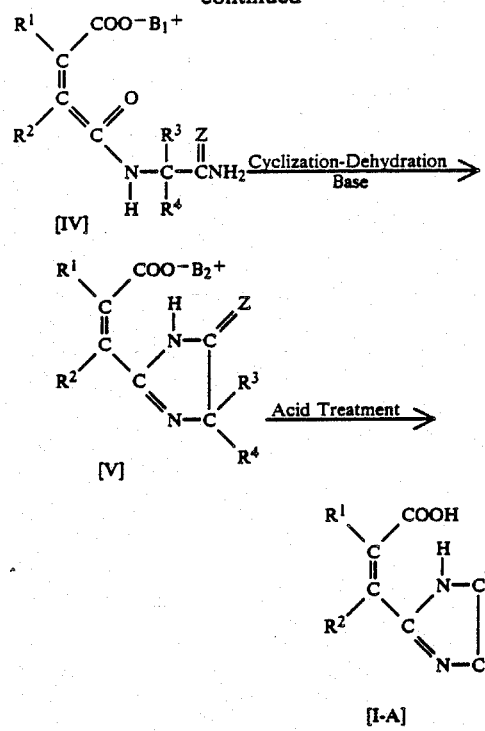

That is, in accordance with Process A, maleic anhydride derivatives represented by the general formula [II] are reacted with amine derivatives represented by the general formula [III] in the presence of a base (containing $B_1$) to form carbamoylacrylic acid derivatives represented by the general formula [IV], these carbamoylacrylic acid derivatives are subjected to a cyclization-dehydration reaction in the presence of a suitable base (containing $B_2$) to form imidazoline derivative salts represented by the general formula [V], and then these imidazoline derivative salts are treated with an acid to form the desired imidazoline derivatives represented by the general formula [I-A]. The imidazoline derivatives represented by the general formula [I-A] are the derivatives of the general formula [I] where M is a hydrogen atom.

In the above reaction, if a suitable solvent selected from compounds such as low boiling ethers (e.g., diethyl ether, tetrahydrofuran and dimethoxyethane), aromatic hydrocarbons (e.g., benzene, toluene and xylene) and lower alcohols (e.g., methyl alcohol and ethyl alcohol) is used in the step of preparing the carbamoylacrylic acid derivatives represented by the general formula [IV], the subsequent reaction is carried out without isolation of the carbamoylacrylic acid derivatives of the general formula [IV]. Preferred examples of such solvents are lower alcohols.

The reaction at each step will hereinafter be explained in detail.

A maleic anhydride derivative represented by the general formula [II] is mixed with 1 to 3 fold equivalent, preferably 1 to 1.5 fold equivalent of an amine derivative represented by the general formula [III] in an inert organic solvent such as low boiling ethers (e.g., diethyl ether, tetrahydrofuran and dimethoxyethane), aromatic hydrocarbons (e.g., benzene, toluene and xylene), lower alcohols, acetonitrile, acetic acid esters and halogenated hydrocarbons in the presence of a base (containing $B_1$) such as tert-amines and alkali metal hydroxides at a temperature of 20° to 60° C., preferably 25° to 30° C., if desired, in an atmosphere of inert gas such as nitrogen. At a stage where the reaction is substantially completed, the product is isolated by usual techniques such as filtration or evaporation of the solvent, or when the solvent is immiscible with water, extraction with a basic water.

The subsequent cyclization-dehydration reaction is carried out in either (a) an organic solvent or (b) an aqueous solution. In a case where the organic solvent (a) is used, the cyclization-dehydration reaction is carried out in a solvent selected from low boiling ethers (e.g., diethyl ether, tetrahydrofuran and dimethoxyethane), aromatic hydrocarbons (e.g., benzene, toluene and xylene), cyclohexane, aprotic polar solvents (e.g., DMSO and DMF) and alcohols (e.g., methyl alcohol and ethyl alcohol) in the presence of a base (containing $B_2$) such as sodium hydride, potassium hydride and sodium alkoxide at a temperature of 30° to 150° C. Preferred examples of bases which can be used are, as well as alkali metal hydrides such as sodium hydride and potassium hydride as described above, alkali metal hydroxides, alkaline earth metal oxides, alkali metal alkoxides, tert-amines (e.g., diisopropylethylamine, 1,5-diazabicyclo[3,4]nonene-5, 1,5-diazodicyclo[5,4,0]undecene-5, 1,4-diazabicyclo[2,2,2]octane and tetramethylguanidine), potassium fluoride, quaternary ammonium hydroxide (e.g., trimethylbenzylammonium hydroxide), and strongly basic ion exchange resins. Preferred examples of solvents which can be used are lower alcohols.

In a case where M in the general formula [I] represents a base residue, the imidazoline derivatives of the present invention are prepared by the above cyclization-dehydration reaction. On the other hand, when M represents a hydrogen atom (that is, the imidazoline derivatives of the present invention are represented by the general formula [I-A], a treatment using an acid such as hydrochloric acid, nitric acid and sulfuric acid is applied to replace the base residue with a hydrogen ion.

In a case where the cyclization-dehydration reaction is carried out in the aqueous solution (b), a carbamoylacrylic acid derivative of the general formula [IV] is reacted directly with about 2.0 to 20.0 mol equivalent of an aqueous solution of sodium hydroxide or potassium hydroxide at a temperature of about 25° to 100° C. for 2 to 6 hours to form an imidazoline derivative salt of the general formula [V] (corresponding to a case in which M of the imidazoline derivatives of the present invention is a base residue) and thereafter, if desired, the reaction mixture is adjusted to about 1.5 to 4.5 in pH to form an imidazoline derivative represented by the general formula [I-A].

When the imidazoline derivative product is insoluble in water, the product is precipitated from an aqueous phase and then recovered by filtration or extraction. On the other hand, when the product is soluble in water, the resulting aqueous solution is extracted with an organic solvent such as ether, methylene chloride and ethyl acetate and the extract thus obtained is then concentrated to obtain the desired imidazoline derivative.

Of the imidazoline derivatives of the present invention, the compounds represented by the general formula [I-A] (that is, M of the general formula [I] is a hydrogen atom) can be prepared by the procedure as described above, and their esters (ester derivatives; i.e., M of the general formula [I] represents an ester residue) and salts (derivative salts; i.e., M of the general formula [I] represents a base residue) can be easily prepared from the imidazoline derivatives of the general formula [I-A] (acid derivatives). That is, ester derivatives can be prepared by reacting the above acid derivatives with an excessive amount of alcohol or its derivatives (e.g., methyl alcohol, ethyl alcohol, propyl alcohol, benzyl alcohol, (2-tetrahydrofuryl)methyl alcohol, 1,1-dimethylallyl alcohol, 2,3-dichloroallyl alcohol and 1-methyl-propargyl alcohol) at a temperature of 50° to 100° C. in the presence of a catalytic amount of mineral acid, such as hydrochloric acid and sulfuric acid, or p-toluenesulfonic acid, for example. Ester derivatives can also be prepared by reacting imidazoline derivatives with halogenated lower alkyl compounds such as methyl iodide in an inert solvent such as acetone and tetrahydrofuran in the presence of an inorganic base such as anhydrous potassium carbonate and anhydrous sodium carbonate to form imidazopyrroline-3,(2H),5-one and then reacting the imidazopyrroline-3,(2H),5-one with at least one equivalent of a suitable alcohol derivatives in the presence of a base such as triethylamine and sodium hydride.

Derivative salts can be prepared by dissolving the above acid derivatives in a suitable solvent and then treating the resulting acid solution with one equivalent of a salt-forming cation. In a case where the salt-forming cation is an inorganic salt (e.g., sodium, potassium, calcium and barium), the acid derivatives are dissolved or dispersed in water or a lower alcohol or a mixture thereof, and one equivalent of a salt-forming cation generally in the form of e.g., hydroxide, carbonate or hydrogencarbonate, preferably in the form of hydroxide is mixed with a solution of the aforementioned acid derivatives. If a precipitate is formed, filtration is applied while on the other hand if no precipitate is formed, the solvent is distilled away under reduced pressure, whereupon inorganic derivative salts (that is, M of the general formula [I] represents a base residue such as alkali metal and alkaline earth metal) can be obtained.

In preparing derivatives wherein M of the general formula [I] represents a base residue such as ammonium and organic ammonium, it suffices that the above acid derivatives are dissolved or dispersed in an organic solvent such as dioxane and tetrahydrofuran and then treated with one equivalent of ammonia, amine or tetraalkylammonium hydroxide. Amines which can be preferably used include isopropylamine, diethylamine, triethylamine, 2-methylallylamine, propargylamine, diethanolamine, ethoxyethylamine, cyclohexylamine, piperidine, morpholine, benzylamine, and benzyltrimethylammonium hydroxide. In this reaction, as in the preparation of the inorganic salts, if a precipitate is formed, filtration is applied while on the other hand if no precipitate is formed, the reaction mixture is concentrated, the solvent still remaining is removed using hexane, and the residue is dried, whereupon derivative salts wherein M of the general formula [I] represents a base residue such as ammonium and organic ammonium can be obtained.

Process B

In accordance with Process B, esters (i.e., M of the general formula [I] or [I'] represents an ester residue) (ester derivatives) among the imidazoline derivatives of the present invention can be prepared efficiently.

This process is carried out according to the following scheme.

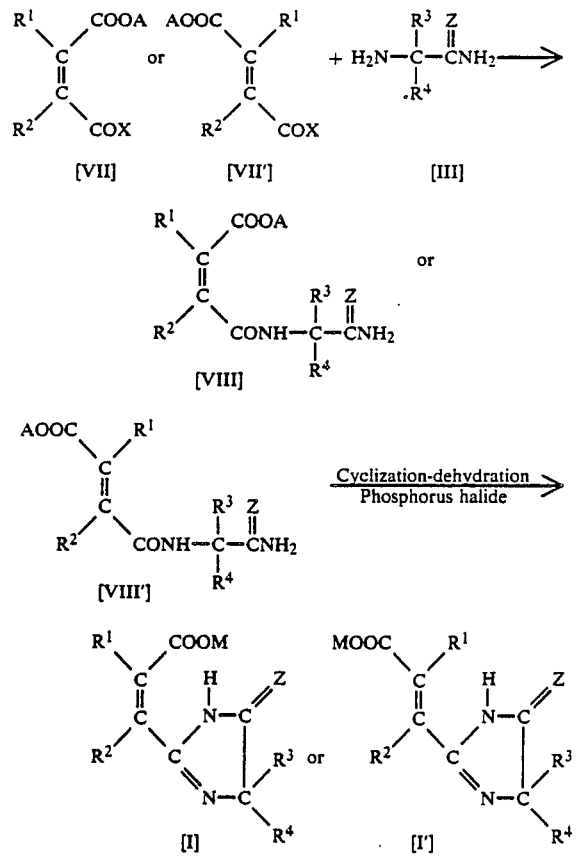

That is, an acid halide represented by the general formula [VII] or [VII'] is reacted with an amine derivative represented by the general formula [III] to form a carbamoylacrylic acid ester derivative represented by the general formula [VIII] or [VIII']. This acid ester derivative is further subjected to cyclization-dehydration using phosphorus halide to obtain the desired imidazoline derivative represented by the general formula [I] or [I'] (wherein M represents an ester residue).

The reaction at each step in Process B will hereinafter be explained in detail.

Acid halides represented by the general formula [VII] or [VII'] as starting material can be prepared by various methods. For example, maleic acid monoester monohalide as an acid halide can be prepared by the following method.

In the first place, maleic anhydride derivative represented by the general formula [II] is reacted with 1 to 10 fold equivalent, preferably 1 to 3 fold equivalent of alcohol, or its derivative or alkali salt in an inert organic solvent selected from low boiling ethers (e.g., diethyl ether, tetrahydrofuran and dimethoxyethane), aromatic hydrocarbons (e.g., benzene, toluene and xylene), acetonitrile, acetic acid esters and halogenated hydrocarbons at a temperature of 0° to 80° C., preferably 0° to 50° C. to form a maleic acid monoester derivative. In the above reaction, alcohol can be used as solvent. Then, to the maleic acid monoester derivative, 1 to 5 fold equivalent, preferably 1 to 3 fold equivalent of thionyl halide (e.g., thionyl chloride, thionyl bromide) or phosphorus halide (phosphorus trihaloride, phosphorus tribromide, phosphorus oxychloride and phosphorus pentachloride) is added, and the resulting mixture is stirred at a temperature of 20° to 80° C. for 1 to 3 hours. In this case, an inert solvent such as aromatic hydrocarbons can be used. Upon distillation under reduced pressure of the solvent or an excess of thionyl halide after the reaction is completed, maleic acid monoester monohalide is obtained as the residue.

Fumaric acid monoester monohalide as an acid halide can be prepared by the following method.

To fumaric acid monoester derivative, 1 to 5 fold equivalent, preferably 1 to 3 fold equivalent of thionyl halide (e.g., thionyl chloride, thionyl bromide) or phosphorus halide (phosphorus trihalide, phosphorus tribromide, phosphorus oxychloride and phosphorus pentachloride) is added, and the resulting mixture is stirred at a temperature of 20° to 80° C. for 1 to 6 hours. In this case, an inert solvent such as aromatic hydrocarbons can be used. Upon distillation under reduced pressure of the solvent or an excess of thionyl halide after the reaction is completed, fumaric acid monoester monohalide is obtained as the residue.

The acid halides of the general formula [VII] or [VII'] as obtained above are reacted with 1 to 1.5 fold equivalent of tert-amines and 1 to 2 fold equivalent, preferably 1 to 1.5 fold equivalent of amines represented by the general formula [III] at a temperature of 0° to 30° C. in a solvent selected from low boiling ethers (e.g., diethyl ether, tetrahydrofuran and dimethoxyethane), aromatic hydrocarbons (e.g., benzene, toluene and xylene), halogenated hydrocarbons (e.g., dichloromethane and chloroform), ketones (e.g., acetone and methyl ethyl ketone and mixtures thereof. Then, upon application of post-treatment by the usual procedure, carbamoylacrylic acid ester derivatives represented by the general formula [VIII] or [VIII'] are obtained.

Subsequently the carbamoylacrylic acid ester derivatives are dissolved or dispersed in an aromatic hydrocarbon solvent or halogenated hydrocarbon solvent and after addition of 1 to 5 fold equivalent, preferably 2 to 3 fold equivalent of phosphorus pentachloride at a temperature of 0° to 20° C., the mixture is heated at a temperature of 20° to 150° C. until the carbamoylacrylic acid ester derivatives are dissolved. After dissolution, hydrochloric acid salts are precipitated and the reaction is completed. These hydrochloric acid salts are obtained by filtration, neutralized with the carbonic acid salts of alkali metals and then subjected to post-treatment by the usual method, whereupon the imidazoline derivatives of the present invention as represented by the general formula [I] or [I'] (wherein M represents an ester residue) can be obtained.

Further, the thus-obtained imidazoline derivatives of the general formula [I] or [I'] (wherein M represents an ester residue) are hydrolyzed to easily obtain the imidazoline derivatives of the general formula [I] or [I'] (wherein M represents a hydrogen or a base residue).

In the above reaction, as well as phosphorus pentachloride, phosphorus oxychloride, phosphorus trichloride or a mixture thereof can be used.

The herbicide or the plant growth regulator of the present invention contains the imidazoline derivatives of the present invention as represented by the general formula [I] or [I'] as the active compound. These compounds are mixed with a liquid carrier such as water or solvents, or a solid carrier such as finely powdered mineral substances, and can be used in a preparation form of a wettable powder, an emulsifiable concentration, a liquid formulation, a floable, a dust and a granule. In this preparation process, surface active agents are added to impart emulsifiability, dispersibility, extendability and so forth.

When the herbicide or the plant growth regulator of the present invention is used in the form of a wettable powder, it is usually prepared by using a composition comprising 10 to 80% by weight (wt%) of an imidazoline derivative of the present invention as an active component, 15 to 88 wt% of a solid carrier and 2 to 5 wt% of a surface active agent. When the herbicide or the plant growth regulator of the present invention is used in the form of an emulsifiable concentration, it is usually prepared by using a composition comprising 20 to 50 wt% of an imidazoline derivative of the present invention as an active component, 35 to 75 wt% of a solvent and 5 to 15 wt% of a surface active agent.

When the herbicide or the plant growth regulator of the present invention is used in the form of a liquid formulation or floable, it is usually prepared by using a composition comprising 20 to 50 wt% of an imidazoline derivative of the present invention as an active component, 35 to 75 wt% of water and 5 to 15 wt% of a surface active agent.

When the herbicide or the plant growth regulator of the present invention is used in the form of a dust, it is usually prepared by compounding 1 to 15 wt% of an imidazoline derivative of the present invention as an active component, 80 to 97 wt% of a solid carrier and 2 to 5 wt% of a surface active agent.

When the herbicide or the plant growth regulator of the present invention is used in the form of a granule, it is usually prepared by compounding 0.2 to 15 wt% of an imidazoline derivative of the present invention as an active component, 80 to 97.8 wt% of a solid carrier and 2 to 5 wt% of a surface active agent.

As such solid carriers, finely powdered mineral substances are used. Examples of these finely powdered mineral substances are oxides such as diatomaceous earth and slaked lime, phosphates such as apatite, sulfates such as gypsum, and silicates such as talc, pyrophyllite, clay, kaolin, bentonite, acid clay, white carbon, quartz powder and silica powder.

Representative examples of organic solvents which are used as solvents are aromatic hydrocarbons such as xylene, toluene and benzene, chlorinated hydrocarbons such as o-chlorotoluene, trichloromethane and trichloroethylene, alcohols such as cyclohexanol, amylalcohol and ethylene glycol, ketones such as isophorone, cyclohexanone and cyclohexenyl-cyclohexanone, ethers such as butylcellosolve, dimethylether and methylethylether, esters such as isopropylacetate, benzylacetate and methylphthalate, amides such as dimethylformamide, and their mixtures.

As surface active agents, any of anionic, nonionic and cationic surface active agents, and amphoteric surface active agents (e.g., amino acid and betaine) can be used.

In the herbicide or the plant growth regulator of the present invention, an imidazoline derivative represented by the general formula [I] or [I'] can be used in combination with other herbicidal or plant growth regulative substances as the active component. Such other herbicidal or plant growth regulative substances include conventinally commercially available herbicides such as phenoxy, diphenyl ether, triazine, urea, carbamate, thiolcarbamate, acid anilide, pyrazole, phosphoric acid, uracil, pyridine, pyridazine, diazine, toluidine, nitrile and sulfonylurea-based herbicides, and plant growth regulators such as maleic hydrazide, mefluidime, flurecol, benazolin, ancymidol and phenoxy type plant growth regulator.

The herbicide or the plant growth regulator of the present invention can be used, if desired, in combination with a herbicide, an insecticide, a fungicide, a plant growth regulator, a fertilizer and the like.

The imidazoline derivatives of the present invention are novel compounds and can be effectively utilized as herbicides or plant growth regulators. The process of the present invention permits preparation of such imidazoline derivatives in high purity and high yield. The herbicide or the plant growth regulator of the present invention, containing the imidazoline derivatives as the effective as the active component can be used in any of foliate treatment and soil treatment. Furthermore the herbicide of the present invention has the features that as compared with conventional herbicides (for example, herbicide disclosed in Japanese Patent Application Laid Open No. 64637/1979), a high herbicidal effect can be obtained in a smaller dose, and furthermore that the weed-killing spectrum is broad and they less phytotoxicity on useful agricultural products. More specifically the herbicide of the present invention exhibits an excellent herbicidal activity against broadleaf weeds such as Ipomoea purpurea, Abutilon theophrasti Xanthium strumarium, Cassia obtusifolia and Amaranthus viridis, Gramineae such as Echinochloa crus-galli, Digitaria sanguinalis, Setaria viridis, Sorghum halepense and Cyperaceae such as Cyperus serotinus, Cyperus rotundus, Cyperus microria and less phytotoxicity on useful agricultural products.

The plant growth regulator of the present invention has features of e.g., producing a high plant growth retarding effect even when used in a small dose, and when used as a growth retarder for various lawn grasses, exhibiting a herbicidal effect simultaneously with a lawn grass growth retarding effect.

The residual period in the soil of the herbicide and plant growth retardant of the present invention is as short as 3 to 4 weeks while on the other hand that containing the known imidazoline derivatives described in Japanese Patent Application Laid-Open No. 64637/1979 is as long as about 3 months and thus the herbicide and plant growth regulator of the present invention are improved over those containing the above known imidazoline derivatives in respect of problems such as environmental pollution and adverse influences on products.

Even when used as a herbicide in non-agricultural fields such as orchard, turf, forest and rail way, the herbicide of the present invention exhibits a high herbicidal activity at a lower dose as compared with the conventional herbicides and furthermore has a broad weed-killing spectrum and exhibits an excellent herbicidal effect against many weeds.

The present invention is described in greater detail with reference to the following examples.

PREPARATION EXAMPLE 1

To a solution of 0.48 grams (g) (3.85 millimoles (mmol)) of 2,3-dimethylmaleic anhydride in 5 milliliters (ml) of anhydrous tetrahydrofuran were added all of 0.50 g (3.85 mmol) of 2-amino-2,3-dimethylbutyramide and 0.6 ml (4.32 mmol) of triethylamine at the same time at room temperature. After 48 hours, white solids which had precipitated were filtered off under reduced pressure, washed with 5 ml of dried tetrahydrofuran and then dried to yield 0.89 g of the triethylammonium salt of amidocarbamoylacrylic acid, an intermediate product for preparation of the compound of the present invention.

Analytical data of the above prepared compound are shown below.

(1) Melting Point: 97.0°–100° C.
(2) Elemental Analysis: $C_{18}H_{35}N_3O_4$:

|  | C (%) | H (%) | N (%) |
|---|---|---|---|
| Found | 60.4 | 10.0 | 11.7 |
| Calculated | 60.5 | 9.8 | 11.8 |

(3) I.R. Absorption Spectrum (KBr tablet method):

| $cm^{-1}$ | Interpretation |
|---|---|
| 1640–1700 | $O=CNH_2$, $O=CNH-$, $O=CO^-$ |
| 2710 | $N^+H(C_2H_5)_3$ |

(4) Proton Nuclear Magnetic Resonance Spectrum (Solvent: $CD_3OD$; Internal Standard: TMS):

| ppm | Interpretation |  |
|---|---|---|
| 0.98 | $CH_3x_2$, | 6H |
| 1.27 | $CH_3x_3$, | 9H |
| 1.42 | $CH_3$, | 3H |
| 1.80 | $CH_3$, | 3H |
| 1.88 | $CH_3$, | 3H |
| 1.7–2.5 | CH, | 1H |
| 3.13 | $CH_2x_3$, | 6H |

PREPARATION EXAMPLE 2

0.48 g (3.85 mmol) of 2,3-dimethylmaleic anhydride, 0.50 g (3.85 mmol) of 2-amino-2,3-dimethyrbutylamide and 0.6 ml (4.32 mmol) of triethylamine were reacted in the same procedure as in Preparation Example 1. After 48 hours, a dispersion of 0.21 g (8.75 mmol) of sodium hydride in 30 ml of dried tetrahydrofuran was slowly added to the reaction mixture without evaporating the tetrahydrofuran solvent, and heated under reflux for 2 hours with stirring.

The reaction mixture was allowed to cool and then quickly cooled with an ice bath. Precipitated yellow solids were filtered off under reduced pressure, washed with 10 ml of dried tetrahydrofuran and then dispersed in a mixture of 50 ml of ethyl acetate and 10 ml of water. The pH of the aqueous layer was adjusted to 4 with 5% aqueous hydrochloric acid solution and after stirring for 2 hours, the aqueous layer was separated.

The aqueous layer was extracted three times with 30 ml of ethyl acetate. These extracts were combined together, washed with saturated brine, dried over sodium sulfate and then concentrated.

Precipitated needle-like crystals were recrystallized from a mixed solvent of methylene chloride and n-hexane to yield 0.23 g of 2,3-dimethyl-3-Z-(4-isopropyl-4-methyl-5-oxo-2-imidazoline-2-yl)acrylic acid, an imidazoline derivative of the present invention.

Analytical data of the above prepared compound are shown in Tables 1 to 3.

PREPARATION EXAMPLE 2A 2.5 g (19.82 mmol) of 2,3-dimethylmaleic anhydride and 2.75 g (21.15 mmol) of 2-amino-2,3-dimethylbutyramide were reacted in the same procedure as in Preparation Example 1 to form 6.97 g (19.50 mmol) of the triethylammonium salt of amidocarbamoylacrylic acid. This salt was dissolved in 100 ml of dried ethanol. To the solution thus prepared was added an ethanol solution of sodium ethoxide prepared from 1.33 g (57.83 mmol) of metallic sodium and 50 ml of dried ethanol while cooling and stirring.

The mixture was heated under reflux for 1 hour, and then the solvent was distilled away under reduced pressure.

The residue was dissolved in 100 ml of water, and when the pH of the aqueous solution was adjusted to pH 3-4 by dropping concentrated hydrochloric acid while cooling, a white precipitate was formed.

After stirring for 30 minutes while cooling, the precipitate was filtered by suction. The precipitate was washed with about 10 ml of cold water and then vacuum dried to yield 3.65 g of the same compound as in Preparation Example 2 (yield: 77.3%).

PREPARATION EXAMPLE 2B 0.48 g (3.85 mmol) of 2,3-dimethylmaleic anhydride was added to a solution of 0.5 g (3.85 mmol) of 2-amino-2,3-dimethylbutyramide and 0.6 ml (4.32 mmol) of triethylamine in 5 ml of dried ethanol while cooling in an ice bath so that the temperature did not exceed 30° C., and then stirred for 1 hour. All of an ethanol solution of sodium ethoxide, prepared by adding 0.20 g (8.70 mmol) of metallic sodium to 5 ml of dried ethanol, was added at the same time to the above solution without isolation of the formed triethylammonium salt of amidocarbamoylacrylic acid, and the resulting mixture was heated under reflux for 1 hour. The solvent was distilled away under reduced pressure, and the residue was treated in the same procedure as in Preparation Example 2A to yield 0.64 g of the same compound as in Preparation Example 2 (yield: 69.9%).

PREPARATION EXAMPLE 3

0.48 g (3.85 mmol) of 2,3-dimethylmaleic anhydride, 0.50 g (3.85 mmol) of 2-amino-2,3-dimethylbutyramide and 0.6 ml (4.32 mmol) of triethylamine were reacted in the same procedure as in Preparation Example 1. The reaction was continued for 48 hours. Then the solvent was distilled away under reduced pressure, and the residue was added to 9.6 ml of a 2N aqueous sodium hydroxide solution (19.2 mmol NaOH) and maintained at 80° C. for 4 hours.

The solution was cooled to room temperature and carefully adjusted to pH 3-4 using concentrated hydrochloric acid while cooling in an ice bath, then extracted with methylene chloride. The extract was washed with saturated brine, dried and then concentrated to yield similar needle-like crystals to those in Preparation Example 2. Analytical data of the crystals are shown below.

(1) Melting Point: 179.0°-179.8° C.
(2) Elemental Analysis:

|  | C (%) | H (%) | N (%) |
|---|---|---|---|
| Found | 60.5 | 7.7 | 11.7 |
| Calculated | 60.5 | 7.6 | 11.8 |

Based on these data, it was confirmed that the formed compound was 2,3-dimethyl-3-Z-(4-isopropyl-4-methyl-5-oxo-2-imidazoline-2-yl)acrylic acid.

PREPARATION EXAMPLE 4

0.50 g (3.96 mmol) of 2,3-dimethylmaleic anhydride, 0.51 g (3.96 mmol) of (2-amino-2-cyclopropyl-propionamide and 0.7 ml (5.04 mmol) of triethylamine were reacted in the same procedure as in Preparation Example 1. After 48 hours, precipitated white solids were filtered off under reduced pressure, washed with 3 ml of dried tetrahydrofuran and then dried. The solids were dissolved in 10 ml of dried ethanol. To the solution thus formed was added 0.27 g (11.88 mmol) of metallic sodium in small portions while cooling in an ice-water bath. The resulting mixture was heated under reflux for 2 hours, and then the ethanol was distilled away under reduced pressure. The residue was diluted with 10 ml of water, and on carefully adjusting to pH 3-4 using concentrated hydrochloric acid, a white precipitate was formed. The mixture was cooled in an ice-water bath for 2 to 3 minutes, and then the white precipitate was filtered with suction, washed with small amounts of water and ethyl ether, and then dried to yield 0.56 g of the desired product (yield: 59.5%). Analytical data of the compound are shown in Tables 1 to 3.

PREPARATION EXAMPLES 5 TO 14

Imidazoline derivatives were prepared from 3.96 mmol of each of the maleic anhydride derivatives shown in Table 1, 3.96 mmol of each of the amine derivatives shown in Table 1 and 0.7 ml of triethylamine in the same procedure as in Preparation Example 4. The analytical data of the compound are shown in Tables 1 to 3.

Compounds (1) to (5) and Compounds (a) to (h) shown in Table 1 are as follows:

2,3-Dimethylmaleic anhydride     Compound (1)

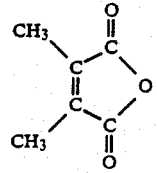

2,3-Diethylmaleic anhydride     Compound (2)

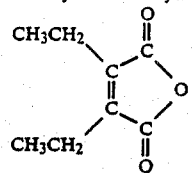

2-Ethyl-3-methylmaleic anhydride     Compound (3)

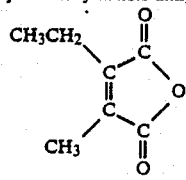

2-n-Butyl-3-methylmaleic anhydride     Compound (4)

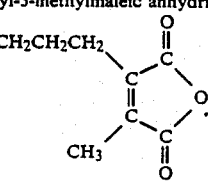

-continued 2,3-di-n-butylmaleic anhydride  Compound (5)
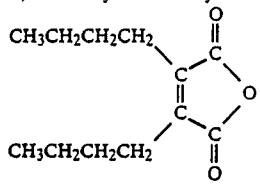

2-Amino-2,3-dimethylbutyramide  Compound (a)
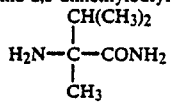

2-Amino-2-methylpropionamide  Compound (b)
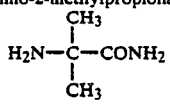

2-Amino-2-methylbutyramide  Compound (c)
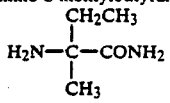

2-Amino-2-n-propylvaleramide  Compound (d)
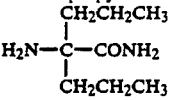

2-Amino-2,4-dimethylvaleramide  Compound (e)
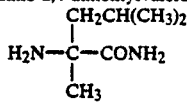

2-Amino-2-cylcohexylpropionamide  Compound (f)
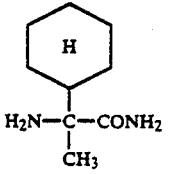

1-Amino-1-carbamoyl-cyclohexane  Compound (g)
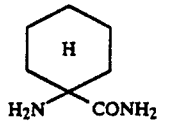

2-Amino-2-cyclopropyl-propionamide  Compound (h)
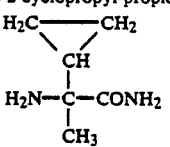

PREPARATION EXAMPLE 15

0.45 g (1.9 mmol) of the 2,3-dimethyl-3-Z-(4-isopropyl-4-methyl-5-oxo-2-imidazoline-2-yl)acrylic acid prepared in Preparation Example 2 was added to a solution of 0.09 g (0.9 mmol) of calcium carbonate and 5 ml of water, and then stirred for 10 minutes. The reaction mixture was filtered by suction, and the filtrate was evaporated to dryness under reduced pressure, washed with dried ether and then dried to yield 0.24 g of the desired product (yield: 50.0%). The analytical data of the compound are shown in Tables 4 to 6.

PREPARATION EXAMPLE 16

The desired product was prepared in the same procedure as in Preparation Example 15 except that 0.08 g (1.9 mmol) of sodium hydroxide was used in place of the calcium carbonate. The analytical data of the compound are shown in Tables 4 to 6.

PREPARATION EXAMPLE 17

0.5 g (2.1 mmol) of the 2,3-dimethyl-3-Z-(4-isopropyl-4-methyl-5-oxo-2-imidazoline-2-yl)acrylic acid prepared in Preparation Example 2 was dissolved in 3 ml of dried tetrahydrofuran. To the solution thus prepared was added 0.12 g (2.1 mmol) of isopropylamine. Upon stirring of the mixture at room temperature for 20 minutes, white solids precipitated. The solids were filtered off with suction, washed with a small amount of dried tetrahydrofuran and then dried to yield 0.6 g of the desired product (yield: 95.8%). The analytical data of the compound are shown in Tables 4 to 6.

PREPARATION EXAMPLES 18 TO 23

The desired product was prepared in the same procedure as in Preparation Example 17 except that 2.1 mmol of each organic amine shown in Table 4 was used in place of the isopropylamine. The analytical data of the compound are shown in Tables 4 to 6.

PREPARATION EXAMPLE 24

(1) Preparation of 2-Isopropyl-2,6,7-trimethyl-5H-imidazo-[1,2-a]pyrroline-3,(2H),5-dione A solution of 2.0 g (8.4 mmol) of 2,3-dimethyl-3-Z-(4-isopropyl-4-methyl-5-oxo-2-imidazoline-2-yl)acrylic acid, 1.28 g (9.26 mmol) of anhydrous potassium carbonate and 2.63 g (18.48 mmol) of methyl iodide in 30 ml of dried acetone was heated under reflux for 1 hour while stirring.

The reaction mixture was allowed to cool. Insoluble solids in the reaction mixture were removed by filtration and washed with 10 ml of acetone. The above filtrate and the washing liquid were combined together and then concentrated. The residue was dissolved in 200 ml of ethyl acetate, and the resulting solution was washed once with 100 ml of distilled water and once with 100 ml of saturated brine, dried over anhydrous sodium sulfate and then concentrated. Precipitated light yellow solids were crystallized from a mixed solvent of diethyl ether and n-hexane to yield 1.26 g of 2-isopropyl-2,6,7-trimethyl-5H-imidazo-[1,2-a]pyrroline-3,(2H),5-dione as colorless prism-like crystals. The analytical data of the compound are shown below.

(1) Melting Point: 96.0°–99.1° C.
(2) Elemental Analysis: $C_{12}H_{16}N_2O_2$

|  | C (%) | H (%) | N (%) |
|---|---|---|---|
| Found | 65.8 | 7.2 | 12.5 |
| Calculated | 65.5 | 7.3 | 12.7 |

(3) I.R. Absorption Spectrum (KBr Tablet Method):

| cm$^{-1}$ | Interpretation |
|---|---|
| 1790, 1720, 1665 | C=O, C=N |

(4) Proton Nuclear Magnetic Resonance Spectrum (Solvent: CDCl$_3$; internal standard: TMS):

| ppm | Interpretation | |
|---|---|---|
| 0.80, 0.96 | CH$_3$x2, | 6H |
| 1.35 | CH$_3$, | 3H |
| 1.93, 2.10 | CH$_3$x2, | 6H |
| 1.97 | CH, | 1H |

(5) Structural Formula:

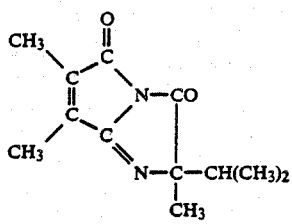

(2) Preparation of Methyl 2,3-Dimethyl-3-Z-(4-isopropyl-4-methyl-5-oxo-2-imidazoline-2-yl)acrylate 2.3 ml (16.5 mmol) of triethylamine was added to a solution of 1.20 g (5.45 mmol) of 2-isopropyl-2,6,7-trimethyl-5H-imidazo-[1,2-a]pyrroline-3(2H),5-dione in 10 ml of methyl alcohol while cooling in an ice bath and stirring in small portions so that the reaction temperature did not exceed 10° C. Then, cooling was stopped and the reaction solution was stirred for 3 hours at room temperature. The methyl alcohol was distilled away from the reaction solution under reduced pressure, and 20 ml of ice water was added to the residue and immediately adjusted to pH 4-6 using 5% aqueous hydrochloric acid solution. The aqueous solution was extracted three times with 30 ml of ethyl acetate, and then the organic layer was washed once with 50 ml of distilled water and once with 50 ml of saturated brine, dried over anhydrous sodium sulfate and concentrated. Precipitated light yellow solids were recrystallized from a mixed solvent of methylene chloride and n-hexane to yield 0.62 g of pure methyl 2,3-dimethyl-3-Z-(4-isopropyl-4-methyl-5-oxo-2-imidazoline-2-yl)acrylate (yield: 44.9%).

The analytical data of the compound are shown in Tables 7 to 9.

PREPARATION EXAMPLE 25

0.46 g (11.4 mmol) of sodium hydride was added to a solution prepared by dissolving 0.83 g (3.77 mmol) of 2-isopropyl-2,6,7-trimethyl-5H-imidazo-[1,2-a]pyrroline-3(2H),5-dione in 5 ml of n-butyl alcohol, while colling in an ice bath and then stirred at room temperature for 20 minutes. Then 20 ml of ethyl acetate and 20 ml of water were added to the reaction solution. An ethyl acetate layer was washed with saturated brine, saturated sodium hydrogencarbonate and saturated brine in this sequence and dried over anhydrous sodium sulfate, and the ethyl acetate was distilled away under reduced pressure. The residue was charged to a silica gel column and eluted with a mixed solvent of toluene and ethyl acetate, then 0.49 g of viscous oily product was obtained (yield: 44.1%).

The analytical data of the compound are shown in Tables 7 to 9.

PREPARATION EXAMPLE 26

1.0 g (6.5 mmol) of 2-isopropyl-3-methylmaleic anhydride, 0.89 g (6.85 mmol) of 2-amino-2,3-dimethylbutyramide and 1.07 ml (7.67 mmol) of triethylamine were reacted in the same procedure as in Preparation Example 1.

After 48 hours, the solvent was removed under reduced pressure and white solid residue was obtained.

The solid was dissolved in 15 ml of driea ethanol.

An ethanol solution of sodium ethoxide prepared from 0.37 g (16.1 mmol) of metallic sodium and 10 ml of anhydrous ethanol was added dropwise to the solution mentioned above while cooling and stirring. The resulting mixture was heated under reflux for 2 hours, and then ethanol was removed under reduced pressure. The residue was dissolved in 20 ml of water, and the pH of the resulting aqueous solution was adjusted to pH 3-4 by dropping concentrated hydrochloric acid, a white precipitate was formed. The white precipitate was filtered by suction, and then dried to yield 1.1 g of desired product (yield: 63.6%) which was 2-isopropyl-3-methyl-3-Z-(4-isopropyl-4-methyl-5-oxo-2-imidazoline-2-yl)acrylic acid.

Analytical data of the product are shown in Tables 7 to 9.

PREPARATION EXAMPLE 27

1 g of crude product was prepared in the same procedure as in Preparation Example 26 except that 1 g (5.15 mmol) of 2-cyclohexyl-3-methylmaleic anhydride, 0.7 g (5.38 mmol) of 2-amino-2,3-dimethylbutyramide, 0.84 ml (6.02 mmol) of triethylamine and 0.3 g (13 mmol) of metallic sodium were used.

The resulting crude product was purified, through a column chromatography using 60 g of silicagel as a packing for separation and a mixture of ethyl acetate and toluene in the volume ratio of 2:1 as a carrier solvent, to yield 0.6 g of the desired product (yield: 38%) which was 2-cyclohexyl-3-methyl-3-Z-(4-isopropyl-4-methyl-5-oxo-2-imidazoline-2-yl)acrylic acid.

Analytical data of the product are shown in Tables 7 to 9.

PREPARATION EXAMPLES 28 AND 29

The desired product was prepared in the same procedure as in Preparation Example 15 except that 0.23 g (1.64 mmol) of potassium carbonate (Preparation Example 28) or 0.07 g (1.64 mmol) of magnesium oxide (Preparation Example 29) was used in place of calcium carbonate.

The analytical data of the product are shown in Tables 4 to 6.

PREPARATION EXAMPLES 30 TO 33

The desired product was prepared in the same procedure as in Preparation Example 17 except that 2.1 mmol of an organic amine shown in Table 4 was used in place of isopropylamine.

The analytical data of the product are shown in Tables 4 to 6.

PREPARATION EXAMPLE 34

The desired product was prepared in the same procedure as in Preparation Example 4 except that 1.1 g (5.87 mmol) of 2-methyl-3-phenyl maleic anhydride, 0.84 g (6.46 mmol) of 2-amino-2,3-dimethylbutyramide, 0.71 g (7.04 mmol) of triethylamine and 0.405 g (17.6 mmol) of metallic sodium were used.

The analytical data of the product are shown in Tables 7 to 9.

PREPARATION EXAMPLE 35

The desired product was prepared in the same procedure as in Preparation Example 4 except that 0.82 g (4.7 mmol) of 2-phenylmaleic anhydride, 0.67 g (5.1 mmol) of 2-amino-2,3-dimethylbutyramide and 0.57 g (5.64 mmol) of triethylamine were used.

The analytical data of the product are shown in Tables 7 to 9.

PREPARATION EXAMPLE 36

1.50 g (10.26 mmol) of 2-amino-2,3-dimethylthiobutyramide and 1.25 g (12.31 mmol) of triethylamine were added at the same time to a solution of 1.29 g (10.26 mmol) of 2,3-dimethylmaleic anhydride dissolved in 20 ml of dried tetrahydrofuran, and then the resulting mixture were stirred at room temperature for 3 days.

After the reaction mixture was concentrated under reduced pressure and the concentrate was dissolved into 20 ml of dried ethanol.

To the solution thus prepared was added while stirring under cooling an ethanol solution of sodium ethylate obtained by reacting 0.71 g (30.87 mmol) of metallic sodium with 20 ml of dried ethanol. The mixture was heated under reflux for 1 hour, and then the solvent was removed under reduced pressure. The residue was dissolved in 100 ml of water, and when the pH of the resulting aqueous solution was adjusted to pH 3–4 by dropping concentrated hydrochloric acid while cooling, a white precipitate was formed. After stirring for 10 minutes while cooling, the precipitate was filtered by suction. The precipitate was washed with about 10 ml of cold water and then vacuum dried to yield 1.33 g of desired product (yield: 51.0%).

The analytical data of the product are shown in Tables 7 to 9.

PREPARATION EXAMPLE 37

6 ml of thionyl chloride was added to 1.03 g (6.52 mmol) of dimethyl fumaric acid monomethyl ester and stirred at room temperature for 4 hours, and then excess of thionyl chloride was removed under reduced pressure.

To the acid halide prepared above was added 10 ml of dried ethyl ether, and the resulting solution was added dropwise to a solution containing 0.85 g (6.54 mmol) of 2-amino-2,3-dimethylbutylamide, 0.725 g (7.18 mmol) of triethylamine, 5 ml of dried ethyl ether and 5 ml of dried acetone, and then stirred at room temperature for 4 hours.

Ethyl ether and acetone were removed from the reaction mixture and water was added thereto to form a precipitate.

The precipitate was filtered by suction and dried to yield 0.84 g of methyl 2,3-dimethyl-E-amidocarbamoyl acrylate (yield: 47.7%).

Meanwhile, the dimethyl fumaric acid monomethyl ester used above was prepared according to a method described in Journal of the American Chemical Society, Vol. 55, page 1585 (1933).

1.64 g of phosphorus pentachloride and 3 ml of toluene were added to methyl-2,3-dimethyl-E-amidocarbamoyl acrylate prepared above and the resulting mixture was stirred at room temperature for 5 hours.

Some amount of water was added to the mixture and the resulting aqueous solution was neutralized by adding sodium hydrogencarbonate, and then the solution was extracted with ethyl acetate to yield 0.7 g of the desired product, methyl 2,3-dimethyl-3-E-(4-isopropyl-4-methyl-5-oxo-2-imidazoline-2-yl)acrylate (yield: 88.1%). This product was purified by recrystallization from dichloromethane n-hexan.

Analytical date of the product are shown in Tables 7 to 9.

TABLE 1

| Preparation Example | No. of Compound prepared | Starting Materials | | Imidazoline Derivative | | | Analytical Data | | |
|---|---|---|---|---|---|---|---|---|---|
| | | Maleic Anhydride Derivative | Amine Derivative | Name of Compound | Yield (%) | Melting Point (°C.) | Elemental Analysis* (%) | | |
| | | | | | | | C | H | N |
| 2 | Compound 1 | Compound (1) | Compound (a) | 2,3-Dimethyl-3-Z-(4-isopropyl-4-methyl-5-oxo-2-imidazoline-2-yl)acrylic acid | 25.0 | 179.0~179.8 | 60.5 (60.5) | 7.6 (7.6) | 11.7 (11.8) |
| 4 | Compound 2 | Compound (1) | Compound (h) | 2,3-Dimethyl-3-Z-(4-cyclopropyl-4-methyl-5-oxo-2-imidazoline-2-yl)acrylic acid | 59.4 | 174.7~188.2 | 61.2 (61.00) | 6.5 (6.82) | 12.0 (11.85) |
| 5 | Compound 3 | Compound (1) | Compound (g) | 2,3-Dimethyl-3-Z-(4,4-pentamethylene-5-oxo-2-imidazoline-2-yl)acrylic acid | 61.0 | 187.2~188.2 | 62.5 (62.38) | 6.9 (7.24) | 11.4 (11.19) |
| 6 | Compound 4 | Compound (1) | Compound (b) | 2,3-Dimethyl-3-Z-(4,4-dimethyl-5-oxo-2-imidazoline-2-yl)acrylic acid | 72.5 | 176.0~178.1 | 57.1 (57.13) | 6.4 (6.71) | 13.7 (13.32) |
| 7 | Compound 5 | Compound (1) | Compound (c) | 2,3-Dimethyl-3-Z-(4-ethyl-4-methyl-5-oxo-2-imidazoline-2-yl)acrylic acid | 55.0 | 158.4~160.6 | 59.4 (58.91) | 6.9 (7.19) | 12.7 (12.49) |
| 8 | Compound 6 | Compound (2) | Compound (a) | 2,3-Diethyl-3-Z-(4-isopropyl-4-methyl-5-oxo-2-imidazoline-2-yl)acrylic acid | 48.0 | 168.8~169.5 | 63.3 (63.13) | 8.1 (8.32) | 10.6 (10.51) |
| 9 | Compound 7 | Compound (5) | Compound (a) | 2,3-Di-n-butyl-3-Z-(4-isopropyl-4-methyl-5-oxo-2-imidazoline-2-yl)acrylic acid | 31.0 | 135.0~136.7 | 67.1 (67.04) | 9.1 (9.37) | 8.5 (8.68) |
| 10 | Compound 8 | Compound (1) | Compound (f) | 2,3-Dimethyl-3-Z-(4-cyclohexyl-4-methyl-5-oxo-2-imidazoline-2-yl)acrylic acid | 69.0 | 159.1~160.5 | 65.3 (64.72) | 7.5 (7.96) | 9.9 (10.06) |
| 11 | Compound 9 | Compound (1) | Compound (d) | 2,3-Dimethyl-3-Z-(4,4-di-n-propyl-5-oxo-2-imidazoline-2-yl)acrylic acid | 49.3 | 132.2~134.8 | 63.3 (63.12) | 8.0 (8.32) | 10.6 (10.51) |
| 12 | Compound 10 | Compound (3) | Compound (a) | 2-Ethyl-3-methyl-3-Z-(4-isopropyl-4-methyl-5-oxo-2-imidazoline-2-yl)acrylic acid | 28.8 | 167.9~168.5 | 61.6 (61.88) | 7.8 (7.98) | 11.1 (11.1) |
| | Compound 11 | Compound (3) | Compound (a) | 3-Ethyl-2-methyl-3-Z-(4-isopropyl-4-methyl-5-oxo-2-imidazoline-2-yl)acrylic acid | 12.2 | 164.2~167.4 | 61.6 (61.88) | 7.8 (7.98) | 11.4 (11.1) |
| 13 | Compound 12 | Compound (1) | Compound (e) | 2,3-Dimethyl-3-Z-(4-isobutyl-4-methyl-5-oxo-2-imidazoline-2-yl)acrylic acid | 79.0 | 145.1~148.1 | 62.0 (61.88) | 7.6 (7.98) | 11.1 (11.1) |
| 14 | Compound 13 | Compound (4) | Compound (a) | 3-n-Butyl-2-methyl-3-Z-(4-isopropyl-4-methyl-5-oxo-2-imidazoline-2-yl)acrylic acid | 33.6 | 162.0~162.8 | 64.5 (64.26) | 8.5 (8.63) | 10.3 (9.99) |
| | Compound 14 | Compound(4) | Compound(a) | 2-n-Butyl-3-methyl-3-Z-(4-isopropyl-4-methyl-5-oxo-2-imidazoline-2-yl)acrylic acid | 16.2 | 146.7~147.4 | 64.4 (64.26) | 8.6 (8.63) | 9.7 (9.99) |

*The values in the parentheses indicate calculated values.

TABLE 2

| Preparation Example | No. of Compound prepared | Structural Formula | Molecular Formula |
|---|---|---|---|
| 2 | Compound 1 | ![structure] CH₃–C(COOH)=C(CH₃)–C(=N–C(CH₃)(CH(CH₃)₂))–NH–CO ring | $C_{12}H_{18}N_2O_3$ |
| 4 | Compound 2 | structure with cyclopropyl-CH group | $C_{12}H_{16}N_2O_3$ |
| 5 | Compound 3 | structure with cyclopentyl group | $C_{13}H_{18}N_2O_3$ |
| 6 | Compound 4 | structure with C(CH₃)₂ | $C_{10}H_{14}N_2O_3$ |
| 7 | Compound 5 | structure with C(CH₃)(CH₂CH₃) | $C_{11}H_{16}N_2O_3$ |
| 8 | Compound 6 | structure with CH₃CH₂ groups and C(CH₃)(CH(CH₃)₂) | $C_{14}H_{22}N_2O_3$ |

TABLE 2-continued

| Preparation Example | No. of Compound prepared | Structural Formula | Molecular Formula |
|---|---|---|---|
| 9 | Compound 7 | (structure with $CH_3CH_2CH_2CH_2$ and $CH_3CH_2CH_2$ substituents, COOH, imidazolinone ring with N=C(CH_3)–CH(CH_3)_2) | $C_{18}H_{30}N_2O_3$ |
| 10 | Compound 8 | (structure with $CH_3$, $CH_3$ substituents, COOH, imidazolinone ring with N=C(CH_3)– cyclohexyl) | $C_{15}H_{22}N_2O_3$ |
| 11 | Compound 9 | (structure with $CH_3$, $CH_3$ substituents, COOH, imidazolinone ring with N=C(CH_2CH_2CH_3)(CH_2CH_2CH_3)) | $C_{14}H_{22}N_2O_3$ |
| 12 | Compound 10 | (structure with $CH_3CH_2$, $CH_3$ substituents, COOH, imidazolinone ring with N=C(CH_3)–CH(CH_3)_2) | $C_{13}H_{20}N_2O_3$ |
|  | Compound 11 | (structure with $CH_3$, $CH_3CH_2$ substituents, COOH, imidazolinone ring with N=C(CH_3)–CH(CH_3)_2) | $C_{13}H_{20}N_2O_3$ |
| 13 | Compound 12 | (structure with $CH_3$, $CH_3$ substituents, COOH, imidazolinone ring with N=C(CH_3)–CH_2CH(CH_3)_2) | $C_{13}H_{20}N_2O_3$ |

TABLE 2-continued

| Preparation Example | No. of Compound prepared | Structural Formula | Molecular Formula |
|---|---|---|---|
| 14 | Compound 13 | (structure with CH₃, COOH, CH₃CH₂CH₂CH₂, N—CO, N—C—CH(CH₃)₂, CH₃) | $C_{15}H_{24}N_2O_3$ |
|  | Compound 14 | (structure with CH₃CH₂CH₂CH₂, COOH, CH₃, N—CO, N—C—CH(CH₃)₂, CH₃) | $C_{15}H_{24}N_2O_3$ |

TABLE 3

| Preparation Example | No. of Compound prepared | Infrared Absorption Spectrum*¹ (cm⁻¹) | | Proton Nuclear Magnetic Resonance Spectrum*² (ppm) |
|---|---|---|---|---|
| 2 | Compound 1 | 1740 | (O=CNH—) | 0.85 (CH₃ × 2, 6H), 1.22 (CH₃, 3H) |
|  |  | 1725 | (O=COH) | 1.72 (CH, 1H), 1.76 (CH₃, 3H), 1.88 (CH₃, 3H), |
|  |  |  |  | 4.41 (NH, 1H), 9.08 (CO₂H, 1H) |
| 4 | Compound 2 | 3345 | (NH) | 0.18, 0.33, 0.47, 1.00, (—CH⟨CH₂/CH₂⟩, 5H), |
|  |  | 1702~1740 | (C=O) | 1.3 (CH₃, 3H), 1.73, 1.84 (CH₃ × 2, 6H), 4.27 (NH, 1H), 9.02 (OH, 1H) |
| 5 | Compound 3 | 3280~3375 | (NH) | 1.52 (⟨hexyl-H⟩, 10H), 1.76 (CH₃, 3H), 1.90 (CH₃, 3H), |
|  |  | 2860~2950 | (CH) |  |
|  |  | 1740~1760 | (C=O) | 4.74 (NH, 1H), 9.06 (OH, 1H) |
| 6 | Compound 4 | 3370 | (NH) | 1.25 (CH₃ × 2, 6H), 1.75 (CH₃, 3H) |
|  |  | 2900~3000 | (CH) | 1.85 (CH₃, 3H), 4.60 (NH, 1H), |
|  |  | 1740~1780 | (C=O) | 9.10 (OH, 1H) |
| 7 | Compound 5 | 3400 | (NH) | 0.85 (CH₃, 3H), 1.25 (CH₃, 3H) |
|  |  | 2920~3000 | (CH) | 1.50 (CH₂, 2H), 1.75 (CH₃, 3H), 1.85 (CH₃, 3H), |
|  |  | 1740~1780 | (C=O) | 4.50 (NH, 1H), 9.15 (OH, 1H) |
| 8 | Compound 6 | 3150~3350 | (NH) | 1.0 (CH₃ × 4, CH, 13H), |
|  |  | 2880~2980 | (CH) | 1.3 (CH₃, 3H), |
|  |  | 1740~1760 | (C=O) | 2.25 (CH₃ × 2, 4H) |
| 9 | Compound 7 | 3310~3350 | (NH) | 0.9 (CH₃ × 4, 12H), 1.2 (CH₃, 3H), |
|  |  | 2880~2980 | (CH) | 1.3 (—CH₂CH₂— × 2, 8H), 1.7 (CH, 1H), |
|  |  | 1740~1760 | (C=O) | 2.2 (CH₃ × 2, 4H), 4.5 (NH, 1H), 9.3 (OH, 1H) |
| 10 | Compound 8 | 3320~3405 | (NH) |  |
|  |  | 2870~2950 | (CH) |  |
|  |  | 1720~1760 | (C=O) | 1.22 (CH₃, 3H), 1.15, 1.68 (⟨hexyl-H⟩, 11H), |
|  |  |  |  | 1.75 (CH₃, 3H), 1.85 (CH₃, 3H), 4.42 (NH, 1H), |
|  |  |  |  | 9.08 (OH, 1H) |
| 11 | Compound 9 | 3370 | (NH) | 0.83, 1.15, 1.47 (CH₂CH₂CH₃ × 2 14H), |
|  |  | 2895~2980 | (CH) | 1.76 (CH₃, 3H), 1.86 (CH₃, 3H), 9.17 (OH, 1H) |
|  |  | 1730~1760 | (C=O) |  |
| 12 | Compound 10 | 3370 | (NH) | 0.82 (CH₃, 3H), 0.85 (CH₃, 3H), 1.02 (CH₃, 3H), |
|  |  | 2900~3000 | (CH) | 1.23 (CH₃, 3H), 1.73 (CH, 1H), 1.87 (CH₃, 3H), |
|  |  | 1738~1770 | (C=O) | 2.21 (CH₂, 2H), 4.4 (NH, 1H), 9.1 (OH, 1H) |
|  | Compound 11 | 3330~3365 | (NH) | 0.82 (CH₃, 3H), 0.86 (CH₃, 3H), 1.10 (CH₃, 3H), |
|  |  | 2895~2990 | (CH) | 1.23 (CH₃, 3H), 1.74 (CH, 1H), 1.78 (CH₃, 3H), |
|  |  | 1730~1770 | (C=O) | 2.26~2.30 (CH₂, 2H), 4.6 (NH, 1H), 9.2 (OH, 1H) |
| 13 | Compound 12 | 3370 | (NH) | 0.83 (CH₃, 3H), 0.90 (CH₃, 3H), 1.23 (CH₃, 3H), |

TABLE 3-continued

| Preparation Example | No. of Compound prepared | Infrared Absorption Spectrum*¹ (cm⁻¹) | | Proton Nuclear Magnetic Resonance Spectrum*² (ppm) |
|---|---|---|---|---|
| 14 | Compound 13 | 2900~3000<br>1740~1770<br>3350<br>2900~3000<br>1762, 1738 | (CH)<br>(C=O)<br>(NH)<br>(CH)<br>(C=O) | 1.42 (CH$_2$, 2H), 1.76 (CH$_3$, 3H), 1.8 (CH, 1H),<br>1.86 (CH$_3$, 3H), 4.48 (NH, 1H), 9.10 (OH, 1H)<br>0.93 (CH$_3$ × 2, 6H), 1.15~1.75 (CH$_3$ × 2, 4H),<br>1.41 (CH$_3$, 3H), 1.95 (CH$_3$, 3H),<br>2.1~2.4 (CH$_2$, 2H) Solvent: CDCl$_3$ |
| " | Compound 14 | 3350<br>2880~2980<br>1730, 1781 | (NH)<br>(CH)<br>(C=O) | 0.93 (CH$_3$ × 2, 6H), 1.37 (CH$_3$, 3H),<br>1.3~1.7 (CH$_2$ × 2, 4H), 1.81 (CH$_3$, 3H),<br>2.0~2.4 (CH$_2$, 2H) Solvent: CDCl$_3$ |

*¹KBr tablet method
*²Solvent: DMSO-d$_6$; internal standard: TMS
In Preparation Example 8, acetone-d$_6$ was used as the solvent.

TABLE 4

| Preparation Example | No. of Compound prepared | Base | Imidazoline Derivative Name of Compound | Yield (%) | Melting Point(°C.) | Analytical Data Elemental Analysis* (%) C | H | N |
|---|---|---|---|---|---|---|---|---|
| 15 | Compound 15 | Calcium carbonate | 2,3-Dimethyl-3-Z-(4-isopropyl-4-methyl-5-oxo-2-imidazoline-2-yl)acrylic acid calcium salt | 50.0 | 94.7~102.2 | 55.8 (56.01) | 6.2 (6.66) | 10.4 (10.89) |
| 16 | Compound 16 | Sodium hydroxide | 2,3-Dimethyl-3-Z-(4-isopropyl-4-methyl-5-oxo-2-imidazoline-2-yl)acrylic acid sodium salt | 85.0 | 69.3~88.1 | 55.5 (55.37) | 6.3 (6.59) | 10.5 (10.77) |
| 17 | Compound 17 | Isopropylamine | 2,3-Dimethyl-3-Z-(4-isopropyl-4-methyl-5-oxo-imidazoline-2-yl)acrylic acid isopropylammonium salt | 95.8 | 132.9~133.8 | 60.3 (60.58) | 9.0 (9.15) | 14.2 (14.13) |
| 18 | Compound 18 | Pyrrolidine | 2,3-Dimethyl-3-Z-(4-isopropyl-4-methyl-5-oxo-2-imidazoline-2-yl)acrylic acid pyrrolidinium salt | 96.3 | 136.8~139.0 | 62.3 (62.11) | 8.4 (8.80) | 13.3 (13.58) |
| 19 | Compound 19 | Cyclohexylamine | 2,3-Dimethyl-3-Z-(4-isopropyl-4-methyl-5-oxo-2-imidazoline-2-yl)acrylic acid cyclohexylammonium salt | 83.3 | 136.7~138.2 | 63.7 (64.06) | 9.4 (9.26) | 12.2 (12.45) |
| 20 | Compound 20 | sec-Butylamine | 2,3-Diethyl-3-Z-(4-isopropyl-4-methyl-5-oxo-2-imidazoline-2-yl)acrylic acid sec-butylammonium salt | 87.3 | 132.6~133.8 | 61.5 (61.71) | 9.1 (9.38) | 13.2 (13.49) |
| 21 | Compound 21 | n-Octylamine | 2,3-Dimethyl-3-Z-(4-isopropyl-4-methyl-5-oxo-2-imidazoline-2-yl)acrylic acid n-octylammonium salt | 85.6 | oily material | 65.6 (65.36) | 10.3 (10.15) | 11.2 (11.43) |
| 22 | Compound 22 | 2-Ethoxypropylamine | 2,3-Dimethyl-3-Z-(4-isopropyl-4-methyl-5-oxo-2-imidazoline-2-yl)acrylic acid 2-ethoxypropylammonium salt | 91.5 | oily material | 59.5 (59.80) | 9.3 (9.14) | 12.1 (12.31) |
| 23 | Compound 23 | Diethanolamine | 2,3-Dimethyl-3-Z-(4-isopropyl-4-methyl-5-oxo-imidazoline-2-yl)acrylic acid diethanolammonium salt | 75.6 | oily material | 55.8 (55.96) | 8.3 (8.51) | 12.1 (12.24) |
| 28 | Compound 28 | Potassium carbonate | 2,3-Dimethyl-3-Z-(4-isopropyl-4-methyl-5-oxo-2-imidazoline-2-yl)acrylic acid potassium salt | 67.5 | hygroscopic solid | 52.2 (52.15) | 6.3 (6.20) | 10.1 (10.14) |
| 29 | Compound 29 | Magnesium oxide | 2,3-Dimethyl-3-Z-(4-isopropyl-4-methyl-5-oxo-2-imidazoline-2-yl)acrylic acid magnesium salt | 100 | hygroscopic solid | 57.5 (57.78) | 6.8 (6.87) | 11.2 (11.23) |
| 30 | Compound 30 | 4-methyl pyperidine | 2,3-Dimethyl-3-Z-(4-isopropyl-4-methyl-5-oxo-2-imidazoline-2-yl)acrylic acid 4-methyl pyperidinium salt | 71.8 | 138.1~140.1 | 64.2 (64.26) | 8.7 (8.99) | 12.4 (12.49) |
| 31 | Compound 31 | 2-amino pyrimidine | 2,3-Dimethyl-3-Z-(4-isopropyl-4-methyl-5-oxo-2-imidazoline-2-yl)acrylic acid 2-amino pyrimidinium salt | 100 | amorphous | 57.4 (57.64) | 6.7 (6.95) | 21.2 (21.01) |
| 32 | Compound 32 | trimethyl-β-hydroxyethyl ammonium salt | 2,3-Dimethyl-3-Z-(4-isopropyl-4-methyl-5-oxo-2-imidazoline-2-yl)acrylic ammonium salt-trimethyl β-hydroxyethyl ammonium salt | 100 | amorphous | 59.6 (59.80) | 9.3 (9.15) | 12.1 (12.31) |
| 33 | Compound 33 | benzyltrimethyl ammonium hydroxide | 2,3-Dimethyl-3-Z-(4-isopropyl-4-methyl-5-oxo-2-imidazoline-2-yl)acrylic acid benzyl trimethyl ammonium salt | 100 | hygroscopic solid | 68.2 (68.19) | 8.3 (8.58) | 10.6 (10.84) |

*The values in the parentheses indicate calculated values.

TABLE 5

| Preparation Example | No. of Compound prepared | Structural Formula | Molecular Formula |
|---|---|---|---|
| 15 | Compound 15 | $\begin{array}{c}CH_3 \quad COO^{\ominus}(Ca^{\oplus})_{\frac{1}{2}} \\ \phantom{CH_3}\diagdown\phantom{xx}\diagup \\ \phantom{xxx}C \\ \phantom{xxx}\| \quad\quad H \\ \phantom{xxx}C\text{—}N\text{—}CO \\ CH_3\diagup\phantom{x}\diagdown\phantom{xx}\diagdown \\ \phantom{xxxxx}C\phantom{xxx}CH(CH_3)_2 \\ \phantom{xxxxx}\|\phantom{xxxx}\| \\ \phantom{xxxxx}N\text{—}C \\ \phantom{xxxxxxxx}\| \\ \phantom{xxxxxxxx}CH_3\end{array}$ | $C_{12}H_{17}N_2O_3 \cdot \frac{1}{2}Ca$ |
| 16 | Compound 16 | (same core structure with $COO^{\ominus}Na^{\oplus}$) | $C_{12}H_{17}N_2O_3Na$ |
| 17 | Compound 17 | (same core structure with $COO^{\ominus}H_3N^{\oplus}\text{—}CH(CH_3)_2$) | $C_{15}H_{27}N_2O_3$ |
| 18 | Compound 18 | (same core structure with $COO^{\ominus}H_2N^{\oplus}\!\!\begin{array}{c}CH_2CH_2\\ \diagdown\\ \diagup\\ CH_2CH_2\end{array}$) | $C_{16}H_{27}N_3O_3$ |
| 19 | Compound 19 | (same core structure with $COO^{\ominus}H_3N^{\oplus}\text{—cyclohexyl}$) | $C_{18}H_{31}N_3O_3$ |
| 20 | Compound 20 | (same core structure with $COO^{\ominus}H_3N^{\oplus}\text{—}CH(CH_3)CH_2CH_3$) | $C_{16}H_{29}N_3O_3$ |

TABLE 5-continued
| Preparation Example | No. of Compound prepared | Structural Formula | Molecular Formula |
|---|---|---|---|
| 21 | Compound 21 | 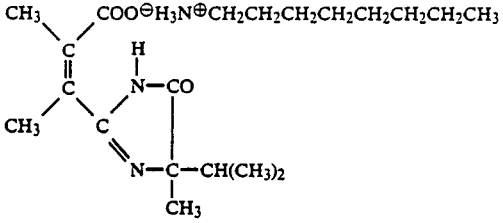 | $C_{20}H_{37}N_3O_3$ |
| 22 | Compound 22 | 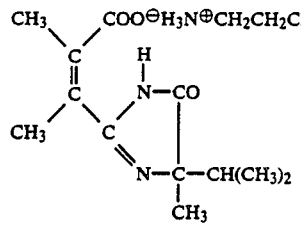 | $C_{17}H_{31}N_3O_4$ |
| 23 | Compound 23 | 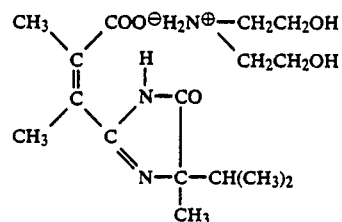 | $C_{16}H_{29}N_3O_3$ |
| 28 | Compound 28 | 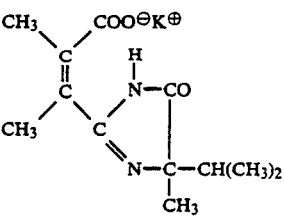 | $C_{12}H_{17}N_2O_3K$ |
| 29 | Compound 29 | 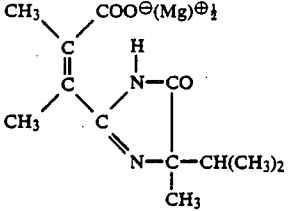 | $C_{12}H_{17}N_2O_3\cdot\tfrac{1}{2}Mg$ |
| 30 | Compound 30 | 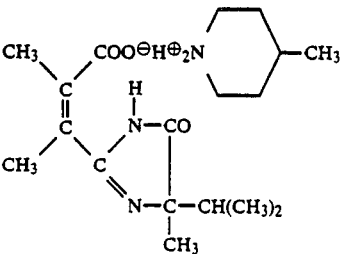 | $C_{18}H_{30}N_3O_3$ |

TABLE 5-continued

| Preparation Example | No. of Compound prepared | Structural Formula | Molecular Formula |
|---|---|---|---|
| 31 | Compound 31 | CH₃, COO⁻H₃N⁺-pyridyl, C=C, CH₃, N-H, CO, C=N-C(CH₃)-CH(CH₃)₂ | $C_{16}H_{23}N_5O_3$ |
| 32 | Compound 32 | CH₃, COO⁻CH₃, ⁺N(CH₃)₂-CH₂CH₂OH, C=C, CH₃, N-H, CO, C=N-C(CH₃)-CH(CH₃)₂ | $C_{17}H_{31}N_3O_4$ |
| 33 | Compound 33 | CH₃, COO⁻CH₃, ⁺N(CH₃)₂-CH₂-phenyl, C=C, CH₃, N-H, CO, C=N-C(CH₃)-CH(CH₃)₂ | $C_{22}H_{33}N_3O_3$ |

TABLE 6

| Preparation Example | No. of Compound prepared | Infrared Absorption Spectrum*¹ (cm⁻¹) | | Proton Nuclear Magnetic Resonance Spectrum*² (ppm) |
|---|---|---|---|---|
| 15 | Compound 15 | 3420 | (NH) | 0.88 (CH₃ × 2, 6H), |
| | | 2880~2960 | (CH) | 1.30 (CH₃, 3H), |
| | | 1690~1730 | (C=O) | 1.98 (CH₃ × 2, 6H) |
| 16 | Compound 16 | 3250~3450 | (NH) | 0.89 (CH₃ × 2, 6H), |
| | | 2750~3000 | (CH) | 1.32 (CH₃, 3H), |
| | | 1685~1738 | (C=O) | 2.00 (CH₃ × 2, 6H) |
| 17 | Compound 17 | 2500~3500 | (CH, NH) | 0.78~1.04 (CH₃ × 2, 6H), 1.26 (CH₃ × 2, 6H), |
| | | 1540~1740 | (C=O) | 1.33 (CH₃, 3H), 1.99, 2.01 (CH₃ × 2, 6H), |
| | | | | 3.41 (CH₃, 1H) |
| 18 | Compound 18 | 3450 | (NH) | 0.90 (CH₃ × 2, 6H), 1.29 (CH₃, 3H), 2.00 (CH₃ × 2, 6H), |
| | | 2720~2970 | (CH) | |
| | | 1700~1735 | (C=O) | 1.85~2.90, 3.28, 5.19 (N⟨pyrrolidine⟩, 8H) |
| 19 | Compound 19 | 2600~3100 | (NH, CH) | 0.92 (CH₃ × 2, 6H), 1.30 (CH₃, 3H), |
| | | 1755~1760 | (C=O) | 1.93 (CH₃ × 2, 6H), 1.98 (CH₃, 3H), |
| | | | | 1.46~2.18 (⟨cyclohexyl-H⟩, CH, 2H) |
| 20 | Compound 20 | 2600~3200 | (NH, CH) | 0.77~1.20, 3.10~3.35 (CH₃ × 2, —CH(CH₃)CH₂CH₃, CH, 16H), |
| | | 1620~1770 | (C=O) | 1.29 (CH₃, 3H), 1.97 (CH₃, 3H), 2.00 (CH₃, 3H) |
| 21 | Compound 21 | 2870~3180 | (NH, CH) | 0.90 (CH₃ × 2, 6H), 1.27 (CH₃, 3H), 2.00 (CH₃ × 2, 6H), |
| | | 1650~1750 | (C=O) | 0.85, 1.38, 2.49 (NCH₂CH₂CH₂CH₂CH₂CH₂CH₂CH₃, 17H) |
| 22 | Compound 22 | 2900~3150 | (NH, CH) | 0.86 (CH₃ × 2, 6H), 1.25 (CH₃, 3H), |
| | | 1650~1740 | (C=O) | 1.83~2.02 (CH₃ × 2, 6H), |
| | | | | 0.74~1.36, 2.52, 3.01, 3.44 (CH₂CH₂CH₂OCH₂CH₃, 11H) |
| 23 | Compound 23 | 2750~3230 | (NH, CH, OH) | 0.89 (CH₃ × 2, 6H), 1.31 (CH₃, 3H), |
| | | 1700~1780 | (C=O) | 1.99 (CH₃ × 2, 6H), 3.11, 3.73 (CH₂CH₂O × 2, 8H) |

TABLE 6-continued

| Preparation Example | No. of Compound prepared | Infrared Absorption Spectrum*[1] (cm$^{-1}$) | | Proton Nuclear Magnetic Resonance Spectrum*[2] (ppm) | |
|---|---|---|---|---|---|
| 28 | Compound 28 | 2250~3600<br>1520~1730 | (NH, CH)<br>(C=O) | 0.84~1.05 (CH$_3$ × 2, 6H)<br>1.30 (CH$_3$, 3H)<br>1.96~2.04 (CH$_3$ × 2, 6H) | methanol d$_4$ |
| 29 | Compound 29 | 2770~3700<br>1540~1740 | (NH, CH)<br>(C=O) | 0.80~1.05 (CH$_3$ × 2, 6H)<br>1.32 (CH$_3$, 3H)<br>1.97 (CH$_3$ × 2, 6H) | methanol d$_4$ |
| 30 | Compound 30 | 2600~3200<br>1740 | (NH, CH)<br>(C=O) | 0.79~1.05 (CH$_3$ × 2, 9H), 1.30 (CH$_3$, 3H)<br>2.0~2.02 (CH$_3$ × 2, 6H)<br>1.45~2.0 (CH$_2$ × 4, 8H) | methanol d$_4$ |
| 32 | Compound 32 | 3300~3600 | (OH) | 0.85, 0.98 (CH$_3$ × 2, 6H), 1.31 (CH$_3$, 3H)<br>1.8~2.1 (CH$_3$ × 2, CH, 7H), 3.23 (N—CH$_3$, × 3, 9H)<br>3.4~4.2 (CH$_3$ × 2, 4H) | methanol d$_4$ |
| 33 | Compound 33 | 2900~3500<br>1580~1720 | (NH, CH)<br>(C=O) | 0.85~1.03 (CH$_3$ × 2, 6H), 1.26 (CH$_3$, 3H),<br>1.97~2.01 (CH$_3$ × 2, 6H), 3.13 (CH$_3$ × 3, 9H),<br>4.59 (CH$_2$, 2H), 7.56 (Ar, 5H) | |

*[1] KBr tablet method
*[2] Solvent: CD$_3$OD; internal standard: TMS
In Preparation Example 28, 29, 30 and 32, methanol-d$_4$ used as the solvent.

TABLE 7

Imidazoline Derivative

| Preparation Example | No. of Compound prepared | Name of Compound | Yield (%) | Melting Point (°C.) | Elemental Analysis* (%) | | | |
|---|---|---|---|---|---|---|---|---|
| | | | | | C | H | N | S |
| 24 | Compound 24 | Methyl 2,3-dimethyl-3-Z-(4-isopropyl-4-methyl-5-oxo-2-imidazoline-2-yl)acrylate | 44.9 | 133.2~134.3 | 61.7 (61.88) | 7.7 (7.99) | 11.1 (11.10) | — |
| 25 | Compound 25 | n-butyl 2,3-dimethyl-3-Z-(4-isopropyl-4-methyl-5-oxo-2-imidazoline-2-yl)acrylate | 44.1 | oily material | 65.4 (65.28) | 8.5 (8.90) | 9.3 (9.52) | — |
| 26 | Compound 26 | 2-isopropyl-3-methyl-3-Z-(4-isopropyl-4-methyl-5-oxo-2-imidazoline-2-yl)acrylic acid | 63.6 | 166.7~167.8 | 63.1 (63.13) | 8.5 (8.33) | 10.2 (10.52) | — |
| 27 | Compound 27 | 2-cyclohexyl-3-methyl-3-Z-(4-isopropyl-4-methyl-5-oxo-2-imidazoline-2-yl)acrylic acid | 38.0 | 187.1~188.9 | 67.0 (66.64) | 8.8 (8.55) | 8.8 (9.14) | — |
| 34 | Compound 34 | 2-phenyl-3-methyl-3-Z-(4-isopropyl-4-methyl-5-oxo-2-imidazoline-2-yl)acrylic acid | 67.6 | 196.3~197.0 | 67.8 (67.98) | 6.6 (6.71) | 9.2 (9.33) | — |
| 35 | Compound 35 | 2-phenyl-3-Z-(4-isopropyl-4-methyl-5-oxo-2-imidazoline-2-yl)acrylic acid | 56.6 | 190.1~191.2 | 67.1 (67.12) | 6.3 (6.34) | 9.6 (9.79) | — |
| 36 | Compound 36 | 2,3-dimethyl-3-Z-(4-isopropyl-4-methyl-5-thiono-2-imidazoline-2-yl)acrylic acid | 51.0 | 173.2~175.0 | 56.7 (56.66) | 7.0 (7.13) | 10.9 (11.02) | 13.8 (12.61) |
| 37 | Compound 37 | methyl 2,3-dimethyl-3-E-(4-isopropyl-4-methyl-5-oxo-2-imidazoline-2-yl)acrylate | 88.1 | 93.5~94.5 | 60.4 (61.88) | 7.7 (7.99) | 11.2 (11.1) | — |

*The values in the parenthses indicate calculated values.

TABLE 8

| Preparation Example | No. of Compound prepared | Structural Formula | Molecular Formula |
|---|---|---|---|
| 24 | Compound 24 | (structure: methyl 2,3-dimethyl-3-Z-(4-isopropyl-4-methyl-5-oxo-2-imidazoline-2-yl)acrylate) | C$_{13}$H$_{20}$N$_2$O$_3$ |
| 25 | Compound 25 | (structure: n-butyl 2,3-dimethyl-3-Z-(4-isopropyl-4-methyl-5-oxo-2-imidazoline-2-yl)acrylate) | C$_{16}$H$_{26}$N$_2$O$_3$ |

TABLE 8-continued
| Preparation Example | No. of Compound prepared | Structural Formula | Molecular Formula |
|---|---|---|---|
| 26 | Compound 26 | 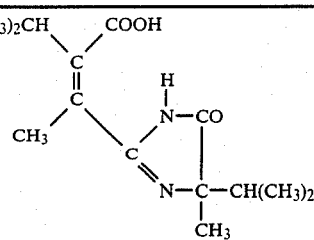 | $C_{14}H_{22}N_2O_3$ |
| 27 | Compound 27 | 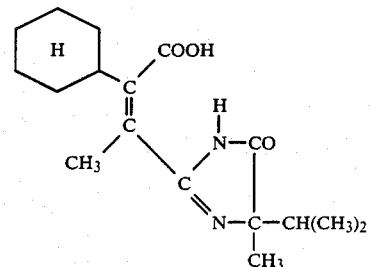 | $C_{17}H_{26}N_2O_3$ |
| 34 | Compound 34 | 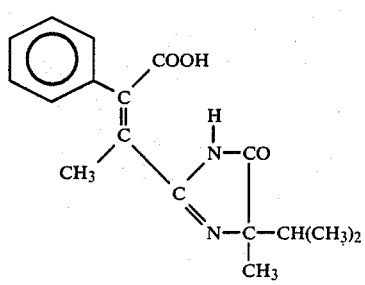 | $C_{17}H_{20}N_2O_3$ |
| 35 | Compound 35 | 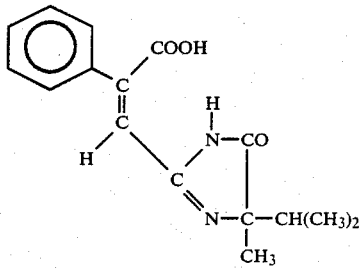 | $C_{16}H_{18}N_2O_3$ |
| 36 | Compound 36 | 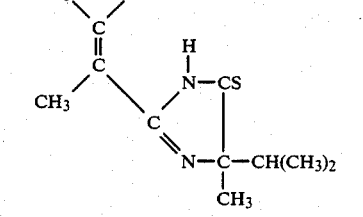 | $C_{12}H_{18}N_2O_2S$ |
| 37 | Compound 37 | 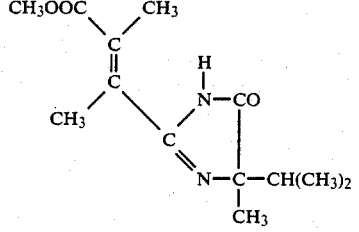 | $C_{13}H_{20}N_2O_3$ |

TABLE 9

| Preparation Example | No. of Compound prepared | Infrared Absorption Spectrum[*1] (cm$^{-1}$) | | Proton Nuclear Magnetic Resonance Spectrum[*2] (ppm) |
|---|---|---|---|---|
| 24 | Compound 24 | 1700~1740 | (NH) | 1.07 (CH$_3$ × 2, 6H), 1.47 (CH$_3$, 3H), 1.84 (CH$_3$, 3H), |
|  |  | 2850~3000 | (CH) | 1.93 (CH$_3$, 3H), 1.74~2.16 (CH, 1H), |
|  |  | 3130~3200 | (C=O) | 3.04 (CH$_3$, 3H), 8.00 (NH, 1H), |
| 25 | Compound 25 | 1730~1780 | (C=O) | 0.80~1.16, 2.88~3.30 (CH$_2$)$_3$CH$_3$, 9H), 1 |
|  |  | 2900~2990 | (CH) | 1.06 (CH$_3$ × 2, 6H), 1.50 (CH$_3$, 3H), |
|  |  | 3100~3400 | (NH) | 1.82 (CH$_3$, 3H), 1.95 (CH$_3$, 3H) |
| 26 | Compound 26 | 3380 | (NH) | 0.94. 0.95 (CH$_3$ × 2, 6H), 1.22 (CH$_3$ × 2, 6H), 1.37 (CH$_3$, 3H), |
|  |  | 2900~3000 | (CH) | 1.97 (CH$_3$, 3H), 1.87 (CH, 1H), 2.84 (CH, 1H), |
|  |  | 1735, 1770 | (C=O) | 4.86 2H Solvent CD$_3$OD |
| 27 | Compound 27 | 3300~3500 | (NH) | 0.93, 0.94 (CH$_3$ × 2, 6H), 1.37 (CH$_3$, 3H), |
|  |  | 2880~3000 | (CH) |  |
|  |  | 1730, 1760 | (C=O) | 1.23~1.9 ( ⟨H⟩—, CH, 11H), 1.98 (CH$_3$, 3H), 2.47 (CH, 1H), 5.88 2H    Solvent: CD$_3$OD |
| 34 | Compound 34 | 3330~3550 | (NH) | 0.85~0.90 (CH$_3$ × 2, 6H), 1.30 (CH$_3$, 3H), 1.75~1.85 (CH, 1H), |
|  |  | 2880~2970 | (CH) |  |
|  |  | 1670~1760 | (C=O) | 2.05 (CH$_3$ × 2, 6H), 4.55 (NH, 1H), 7.50 ( ⟨○⟩—, 5H), 9.25 (COOH, 1H)    DMSO-d$_6$ |
| 35 | Compound 35 | 2500~3500 | (NH, CH) | 0.75~0.95 (CH$_3$ × 2, 6H), 1.20 (CH$_3$, 3H), 1.80~1.90 (CH, 1H), |
|  |  | 1600~1740 | (C=O) | 6.55 (=CH—, 1H), 7.45~7.55 ( ⟨○⟩—, 5H), |
| 36 | Compound 36 | 2990~3300 | (NH, CH) | 0.80~1.02 (CH$_3$ × 2, 6H), |
|  |  | 1750~1775 | (C=O) | 1.41 (CH$_3$, 3H), |
|  |  |  |  | 1.85~1.95 (CH$_3$ × 2, 6H) |
| 37 | Compound 37 | 3100 | (NH) | 0.86, 1.06 (CH$_3$ × 2, 6H), 1.35 (CH$_3$, 3H), |
|  |  | 2900~3000 | (CH) | 2.02 (CH, 1H), 2.08 (CH$_3$, 3H), 2.17 (CH$_3$, 3H), |
|  |  | 1740~1750 | (C=O) | 3.80 (OCH$_3$, 3H), |

[*1]Kbr tablet method
[*2]Solvent: DMSO-d$_6$: internal standard: TMS

EXAMPLES AND COMPARATIVE EXAMPLE

(1) Preparation of Herbicide or Plant Growth Regulator 97 parts by weight of talc (trade name: Zeaklite) as a carrier, 1.5 parts by weight of alkylarylsulfonate as a surfactant (trade name: Neo pelex, produced by Kao Atlas Co., Ltd.) and 1.5 parts by weight of a mixture of nonionic and anionic type surfactant (trade name: Sorpol 800 A, produced to Toho Kagaku Kogyo Co., Ltd.) were uniformly pulverized and mixed to form a carrier for a wettable powder. Then, 90 parts by weight of the above carrier and 10 parts by weight of each compound (imidazoline derivative) shown in Table 10 were uniformly pulverized and mixed to form a herbicide or a plant growth regulator.

(2) Biological Test (Foliate Treatment Test)

Seeds of *Echinochloa crus-galli, Digitaria senguinalis, Ipomoea purpurea, Raphanas sativa* and *Abutilon theophrasti* were sown in a 1/2000-arc wagner pot charged with field soil, covered with soil and grown in a greenhouse. At the first- or second-leaf stage of the plants, a predetermined amount of the herbicide prepared in (1) above was suspended in water and uniformly sprayed to the foliate in an amount of 100 liters per 10 ares. Thereafter the plants were grown in the greenhouse. At the 20th day from the spray treatment, the herbicidal effect was determined according to the criteria shown below. The results are shown in Table 10.

Determination Criteria

| Symbol | Herbicidal Effect (Weed-Killing Rate) |
|---|---|
| 0 | Less than 5% (almost no effect) |
| 1 | 5 to 20% |
| 2 | 20 to 40% |
| 3 | 40 to 70% |
| 4 | 70 to 90% |
| 5 | not less than 90% (almost all died) |

The weed-killing rate was determined by the following equation:

$$\text{Weed-Killing Rate (\%)} = \left(1 - \frac{A}{B}\right) \times 100$$

wherein
A = fresh weight of aerial part of weeds treated with herbicide, and
B = fresh weight of aerial part of weeds not treated with herbicide

(3) Biological Test (Soil Treatment Test)

Seeds of *Echinochloa crus-galli, Digitaria sanguinalis, Ipomoea purpurea Raphanas sative* and *Abutilon theophrasti* were sown in a 1/2000 are wagner pot charged with field soil, covered with soil, and then a predetermined amount of each herbicide prepared using each compound shown in Table 11 in the same manner as in (1) above was suspended in water and uniformly sprayed on the soil surface. After spraying, the plants were grown in a greenhouse. At the 20th day from the spray treatment, the herbicidal effect was determined according to the same criteria as in (2) above. The results are shown in Table 11.

(4) Biological Test (Test for growth retardant of turf)

Turf (*Zoysia matrella*) was transplanted in a 1/5000 are wagner pot and then the pot was kept in a greenhouse until the turf grew up uniformly all over the pot.

After growing up, the turf was cut into 2 cm in the length thereof.

A predetermined amount of the plant growth regulator prepared in (1) above was suspended in water and uniformly sprayed to the foliate of the turf in an amount of 100 liters per 10 ares.

At a month from the spray treatment, a plant growth retarding effect was evaluated according to the following equation.

$$\text{Plant Growth Retarding Ratio (\%)} = \left(1 - \frac{C}{D}\right) \times 100$$

wherein
C = length of the turf treated with plant growth retardant, and
D = length of the turf not treated with plant growth retardant.

The results are shown in Table 12.

TABLE 10

| No. | Compound as active component | Amount of herbicide (Kg.a.i./ha) | Herbicidal effect | | | | |
|---|---|---|---|---|---|---|---|
| | | | *Echinochloa crus-galli* | *Digitaria sanguinalis* | *Ipomoea purpurea* | *Raphanas sativa* | *Abutilon theophrasti* |
| Example 1 | Compound 1 | 1 | 5 | 5 | 5 | 5 | 5 |
| | | 0.5 | 5 | 5 | 5 | 5 | 5 |
| | | 0.25 | 5 | 5 | 5 | 5 | 5 |
| Example 2 | Compound 2 | 1 | 5 | 5 | 5 | 5 | 4 |
| | | 0.5 | 4 | 5 | 4 | 5 | 4 |
| | | 0.25 | 3 | 5 | 3 | 5 | 3 |
| Example 3 | Compound 3 | 1 | 3 | 2 | 3 | 4 | 0 |
| | | 0.5 | 2 | 1 | 1 | 3 | 0 |
| Example 4 | Compound 4 | 1 | 3 | 5 | 4 | 5 | 4 |
| | | 0.5 | 1 | 4 | 3 | 5 | 2 |
| Example 5 | Compound 5 | 1 | 5 | 5 | 5 | 5 | 5 |
| | | 0.5 | 5 | 5 | 4 | 5 | 2 |
| | | 0.25 | 4 | 5 | 2 | 5 | 1 |
| Example 6 | Compound 6 | 1 | 2 | 2 | 1 | 5 | 1 |
| | | 0.5 | 0 | 0 | 0 | 5 | 0 |
| Example 7 | Compound 10 | 1 | 3 | 5 | 2 | 5 | 1 |
| | | 0.5 | 1 | 4 | 2 | 5 | 0 |
| Example 8 | Compound 11 | 1 | 5 | 5 | 3 | 5 | 3 |
| | | 0.5 | 5 | 5 | 3 | 5 | 3 |
| | | 0.25 | 3 | 4 | 1 | 5 | 2 |
| Example 9 | Compound 14 | 1 | 1 | 3 | 2 | 5 | 0 |
| | | 0.5 | 0 | 1 | 1 | 5 | 0 |
| Example 10 | Compound 15 | 1 | 5 | 5 | 5 | 5 | 5 |
| | | 0.5 | 5 | 5 | 5 | 5 | 5 |
| | | 0.25 | 5 | 5 | 5 | 5 | 5 |
| Example 11 | Compound 16 | 1 | 5 | 5 | 5 | 5 | 5 |
| | | 0.5 | 5 | 5 | 5 | 5 | 5 |
| | | 0.25 | 5 | 5 | 5 | 5 | 5 |
| Example 12 | Compound 17 | 1 | 5 | 5 | 5 | 5 | 5 |
| | | 0.5 | 5 | 5 | 5 | 5 | 5 |
| | | 0.25 | 5 | 5 | 5 | 5 | 5 |
| Example 13 | Compound 18 | 1 | 5 | 5 | 5 | 5 | 5 |
| | | 0.5 | 5 | 5 | 5 | 5 | 5 |
| | | 0.25 | 5 | 5 | 5 | 5 | 5 |
| Example 14 | Compound 19 | 1 | 5 | 5 | 5 | 5 | 5 |
| | | 0.5 | 5 | 5 | 5 | 5 | 5 |
| | | 0.25 | 4 | 5 | 4 | 5 | 4 |
| Example 15 | Compound 20 | 1 | 5 | 5 | 5 | 5 | 5 |
| | | 0.5 | 5 | 5 | 5 | 5 | 5 |
| | | 0.25 | 5 | 5 | 5 | 5 | 5 |
| Example 16 | Compound 21 | 1 | 2 | 2 | 1 | 5 | 0 |
| | | 0.5 | 0 | 0 | 0 | 5 | 0 |
| Example 17 | Compound 22 | 1 | 3 | 1 | 1 | 5 | 0 |
| | | 0.5 | 2 | 0 | 0 | 5 | 0 |
| Example 18 | Compound 23 | 1 | 5 | 5 | 5 | 5 | 5 |
| | | 0.5 | 5 | 5 | 4 | 5 | 4 |
| Example 19 | Compound 24 | 1 | 2 | 4 | 2 | 5 | 1 |
| | | 0.5 | 1 | 1 | 0 | 5 | 0 |
| Example 20 | Compound 25 | 1 | 1 | 4 | 1 | 5 | 1 |
| | | 0.5 | 1 | 4 | 0 | 5 | 0 |
| Example 21 | Compound 28 | 1 | 5 | 5 | 5 | 5 | 5 |
| | | 0.5 | 5 | 5 | 5 | 5 | 5 |
| | | 0.25 | 5 | 5 | 5 | 5 | 5 |
| Example 22 | Compound 29 | 1 | 5 | 5 | 5 | 5 | 5 |
| | | 0.5 | 5 | 5 | 5 | 5 | 5 |
| | | 0.25 | 5 | 5 | 5 | 5 | 5 |
| Example 23 | Compound 30 | 1 | 5 | 5 | 5 | 5 | 5 |

TABLE 10-continued

| No. | Compound as active component | Amount of herbicide (Kg.a.i./ha) | Herbicidal effect | | | | |
|---|---|---|---|---|---|---|---|
| | | | Echinochloa crus-galli | Digitaria sanguinalis | Ipomoea purpurea | Raphanas sativa | Abutilon theophrasti |
| | | 0.5 | 5 | 5 | 5 | 5 | 5 |
| | | 0.25 | 5 | 5 | 5 | 5 | 5 |
| Example 24 | Compound 31 | 1 | 5 | 5 | 5 | 5 | 5 |
| | | 0.5 | 5 | 5 | 5 | 5 | 5 |
| | | 0.25 | 5 | 5 | 5 | 5 | 4 |
| Example 25 | Compound 32 | 1 | 5 | 5 | 5 | 5 | 5 |
| | | 0.5 | 5 | 5 | 5 | 5 | 5 |
| | | 0.25 | 5 | 5 | 5 | 5 | 4 |
| Example 26 | Compound 33 | 1 | 5 | 5 | 5 | 5 | 5 |
| | | 0.5 | 5 | 5 | 5 | 5 | 5 |
| | | 0.25 | 5 | 5 | 5 | 5 | 5 |
| Example 27 | Compound 34 | 1 | 2 | 2 | 4 | 5 | 2 |
| | | 0.5 | 0 | 2 | 3 | 5 | 1 |
| Example 28 | Compound 36 | 1 | 5 | 5 | 5 | 5 | 5 |
| | | 0.5 | 5 | 5 | 5 | 5 | 5 |
| | | 0.25 | 4 | 5 | 5 | 5 | 4 |
| Example 29 | Compound 37 | 1 | 5 | 5 | 5 | 5 | 5 |
| | | 0.5 | 4 | 5 | 5 | 5 | 3 |
| Comparative Example | Formula (A)* | 1 | 0 | 1 | 2 | 5 | 2 |
| | | 0.5 | 0 | 0 | 1 | 5 | 1 |
| | | 0.25 | 0 | 0 | 0 | 2 | 0 |

Formula (A)*

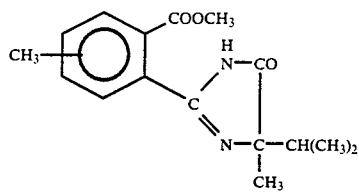

TABLE 11

| No. | Compound as active component | Amount of herbicide (Kg.a.i./ha) | Herbicidal effect | | | | |
|---|---|---|---|---|---|---|---|
| | | | Echinochloa crus-galli | Digitaria sanguinalis | Ipomoea purpurea | Raphanas sativa | Abutilon theophrasti |
| Example 30 | Compound 1 | 1 | 5 | 5 | 5 | 5 | 5 |
| | | 0.5 | 5 | 5 | 5 | 5 | 5 |
| | | 0.25 | 5 | 5 | 5 | 5 | 5 |
| Example 31 | Compound 2 | 4 | 5 | 5 | 5 | 5 | 4 |
| | | 2 | 5 | 5 | 4 | 5 | 3 |
| | | 1 | 5 | 4 | 2 | 5 | 2 |
| Example 32 | Compound 3 | 4 | 5 | 4 | 5 | 5 | 3 |
| | | 2 | 3 | 2 | 5 | 5 | 1 |
| | | 1 | 1 | 1 | 2 | 5 | 0 |
| Example 33 | Compound 4 | 4 | 1 | 1 | 1 | 4 | 3 |
| | | 2 | 0 | 0 | 0 | 3 | 3 |
| | | 1 | 0 | 0 | 0 | 3 | 2 |
| Example 34 | Compound 5 | 4 | 5 | 5 | 3 | 5 | 5 |
| | | 2 | 5 | 5 | 2 | 5 | 5 |
| | | 1 | 5 | 5 | 2 | 5 | 2 |
| Example 35 | Compound 6 | 4 | 5 | 3 | 3 | 5 | 3 |
| | | 2 | 5 | 2 | 2 | 5 | 1 |
| | | 1 | 3 | 1 | 1 | 5 | 0 |
| Example 36 | Compound 10 | 4 | 5 | 5 | 3 | 5 | 2 |
| | | 2 | 4 | 5 | 2 | 5 | 1 |
| | | 1 | 3 | 4 | 2 | 5 | 0 |
| Example 37 | Compound 13 | 4 | 1 | 1 | 3 | 4 | 0 |
| | | 2 | 0 | 0 | 1 | 3 | 0 |
| | | 1 | 0 | 0 | 0 | 3 | 0 |
| Example 38 | Compound 14 | 4 | 5 | 5 | 3 | 5 | 2 |
| | | 2 | 5 | 3 | 2 | 5 | 1 |
| | | 1 | 3 | 3 | 2 | 5 | 0 |
| Example 39 | Compound 15 | 4 | 5 | 5 | 4 | 5 | 4 |
| | | 2 | 5 | 5 | 3 | 5 | 3 |
| | | 1 | 5 | 5 | 2 | 5 | 3 |
| Example 40 | Compound 16 | 4 | 5 | 5 | 5 | 5 | 5 |
| | | 2 | 5 | 5 | 5 | 5 | 5 |
| | | 1 | 5 | 5 | 5 | 5 | 5 |
| Example 41 | Compound 17 | 4 | 5 | 5 | 5 | 5 | 4 |
| | | 2 | 5 | 5 | 5 | 5 | 3 |
| | | 1 | 5 | 5 | 5 | 5 | 3 |
| Example 42 | Compound 18 | 4 | 5 | 5 | 5 | 5 | 5 |
| | | 2 | 5 | 5 | 5 | 5 | 5 |
| | | 1 | 5 | 5 | 3 | 5 | 3 |
| Example 43 | Compound 19 | 4 | 5 | 5 | 5 | 5 | 4 |

TABLE 11-continued

| No. | Compound as active component | Amount of herbicide (Kg.a.i./ha) | Herbicidal effect | | | | |
|---|---|---|---|---|---|---|---|
| | | | Echinochloa crus-galli | Digitaria sanguinalis | Ipomoea purpurea | Raphanas sativa | Abutilon theophrasti |
| | | 2 | 5 | 5 | 5 | 5 | 3 |
| | | 1 | 5 | 5 | 3 | 5 | 3 |
| Example 44 | Compound 20 | 4 | 5 | 5 | 5 | 5 | 5 |
| | | 2 | 5 | 5 | 5 | 5 | 4 |
| | | 1 | 5 | 5 | 5 | 5 | 4 |
| Example 45 | Compound 21 | 4 | 4 | 5 | 3 | 5 | 3 |
| | | 2 | 3 | 4 | 1 | 4 | 2 |
| | | 1 | 1 | 2 | 0 | 2 | 2 |
| Example 46 | Compound 23 | 4 | 5 | 5 | 4 | 5 | 4 |
| | | 2 | 5 | 5 | 3 | 5 | 3 |
| | | 1 | 5 | 5 | 3 | 5 | 3 |
| Example 47 | Compound 24 | 4 | 5 | 5 | 4 | 5 | 3 |
| | | 2 | 4 | 4 | 4 | 5 | 2 |
| | | 1 | 3 | 4 | 3 | 5 | 2 |
| Example 48 | Compound 25 | 4 | 4 | 4 | 3 | 5 | 4 |
| | | 2 | 2 | 2 | 1 | 5 | 3 |
| | | 1 | 2 | 2 | 0 | 5 | 2 |
| Example 49 | Compound 26 | 4 | 4 | 3 | 3 | 4 | 3 |
| | | 2 | 4 | 1 | 2 | 3 | 2 |
| | | 1 | 2 | 0 | 0 | 1 | 1 |
| Example 50 | Compound 28 | 4 | 5 | 5 | 5 | 5 | 4 |
| | | 2 | 5 | 5 | 4 | 5 | 3 |
| | | 1 | 5 | 5 | 3 | 5 | 3 |
| Example 51 | Compound 29 | 4 | 5 | 5 | 5 | 5 | 5 |
| | | 2 | 5 | 5 | 5 | 5 | 4 |
| | | 1 | 5 | 5 | 4 | 5 | 3 |
| Example 52 | Compound 30 | 4 | 5 | 5 | 5 | 5 | 5 |
| | | 2 | 5 | 5 | 5 | 5 | 5 |
| | | 1 | 5 | 5 | 4 | 5 | 4 |
| Example 53 | Compound 31 | 4 | 5 | 5 | 5 | 5 | 5 |
| | | 2 | 5 | 5 | 4 | 5 | 4 |
| | | 1 | 5 | 5 | 4 | 5 | 4 |
| Example 54 | Compound 32 | 4 | 5 | 5 | 5 | 5 | 5 |
| | | 2 | 5 | 5 | 4 | 5 | 4 |
| | | 1 | 4 | 5 | 2 | 5 | 3 |
| Example 55 | Compound 33 | 4 | 5 | 5 | 5 | 5 | 5 |
| | | 2 | 5 | 5 | 4 | 5 | 4 |
| | | 1 | 5 | 5 | 4 | 5 | 3 |
| Example 56 | Compound 34 | 4 | 4 | 4 | 5 | 5 | 4 |
| | | 2 | 3 | 4 | 5 | 5 | 2 |
| | | 1 | 2 | 2 | 4 | 4 | 1 |
| Example 57 | Compound 36 | 4 | 5 | 5 | 5 | 5 | 5 |
| | | 2 | 5 | 5 | 4 | 5 | 5 |
| | | 1 | 5 | 5 | 4 | 5 | 4 |
| Example 58 | Compound 37 | 4 | 4 | 5 | 4 | 5 | 4 |
| | | 2 | 4 | 4 | 4 | 5 | 3 |
| | | 1 | 2 | 3 | 2 | 4 | 2 |

TABLE 12

| No. | Compound as active component | Amount of plant growth retardant (kg.a.i./ha) | Plant growth retarding effect | | |
|---|---|---|---|---|---|
| | | | Length of turf (cm) | Plant growth retarding ratio (%) | Phytotoxicity |
| Example 59 | Compound 1 | 2 | 2 | 87 | no |
| | | 1 | 2 | 87 | no |
| | | 0.5 | 2 | 87 | no |
| | | 0.25 | 2 | 87 | no |
| Example 60 | Compound 2 | 0.25 | 4 | 73 | no |
| Example 61 | Compound 5 | 0.25 | 2 | 87 | no |
| Example 62 | Compound 11 | 0.25 | 2 | 87 | no |
| Example 63 | Compound 15 | 0.25 | 2 | 87 | no |
| Example 64 | Compound 16 | 0.25 | 2 | 87 | no |
| Example 65 | Compound 17 | 0.25 | 2 | 87 | no |
| Example 66 | Compound 18 | 0.25 | 2 | 87 | no |
| Example 67 | Compound 19 | 0.25 | 2 | 87 | no |
| Example 68 | Compound 20 | 0.25 | 2 | 87 | no |
| Example 69 | Compound 22 | 0.25 | 8 | 47 | no |
| Example 70 | Compound 23 | 0.25 | 2 | 87 | no |
| Example 71 | Compound 24 | 0.25 | 11 | 27 | no |
| Example 72 | Compound 28 | 0.25 | 2 | 87 | no |
| Example 73 | Compound 29 | 0.25 | 2 | 87 | no |
| Example 74 | Compound 30 | 0.25 | 2 | 87 | no |
| Example 75 | Compound 31 | 0.25 | 2 | 87 | no |
| Example 76 | Compound 33 | 0.25 | 2 | 87 | no |
| Example 77 | Compound 36 | 0.25 | 2 | 87 | no |
| Example 78 | Compound 37 | 0.25 | 4 | 73 | no |
| Comparative | known compound* | 0.5 | 3 | 80 | no |

TABLE 12-continued

| No. | Compound as active component | Amount of plant growth retardant (kg.a.i./ha) | Length of turf (cm) | Plant growth retarding ratio (%) | Phytotoxicity |
|---|---|---|---|---|---|
| Example | | 0.25 | 12 | 20 | no |
| Comparative Example | not-treated | — | 15 | 0 | no |

*trade name: Embark produced by Nissan Kagaku Kogyo Co. Ltd.

What is claimed is:

1. An imidazoline compound represented by the formula:

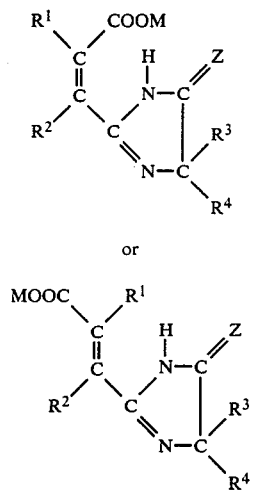

wherein $R^1$ and $R^2$ each represent a hydrogen atom, a lower alkyl group, a $C_3$–$C_6$ cycloalkyl group or a phenyl group, $R^3$ and $R^4$ each represent a lower alkyl group, a $C_3$–$C_6$ cycloalkyl group or a $C_3$–$C_6$ cycloalkyl group in which $R^3$ and $R^4$ are bonded together, Z represents an oxygen atom or a sulfur atom, and M represents a hydrogen atom, a base residue or an ester residue wherein
  said base residue is an alkali metal, an alkaline earth metal or an organic ammonium cation;
  said ester residue is $C_1$–$C_{12}$ alkyl; $C_1$–$C_{12}$ alkyl substituted with $C_1$–$C_{13}$ alkoxy, $C_3$–$C_6$ cycloalkyl, halogen, $C_1$–$C_3$ thioalkyl, phenyl or furyl; $C_3$–$C_5$ alkenyl; a halogen-substituted $C_3$–$C_5$ alkenyl; phenyl-substituted $C_3$–$C_5$ alkenyl; $C_3$–$C_5$ alkynyl; phenyl-substituted $C_3$–$C_5$ alkynyl; a hydroxyl substituted $C_3$–$C_5$ alkynyl; and a substituted phenyl group having substituents selected from the group consisting of halogen, methyl and methoxy.

2. The compound of claim 1 wherein $R_1$ is hydrogen, $C_1$–$C_4$ alkyl, $C_3$–$C_6$ cycloalkyl or phenyl;
$R^2$ is hydrogen, $C_1$–$C_4$ alkyl, $C_3$–$C_6$ cycloalkyl or phenyl;
$R^3$ is $C_1$–$C_4$ alkyl, $C_3$–$C_6$ cycloalkyl, $R_4$ is $C_1$–$C_4$ alkyl, $C_3$–$C_6$ cycloalkyl, or $R^3$ and $R^4$ are bonded together to form a $C_3$–$C_6$ cycloalkyl;
Z is oxygen or sulfur;
M is hydrogen; said alkali metal ion; said alkaline earth metal ion, or said organic ammonium cation; a $C_1$–$C_{12}$ alkyl; a $C_1$–$C_{12}$ alkyl substituted with a $C_1$–$C_3$ alkoxy, $C_3$–$C_6$ cycloalkyl, halogen atoms, $C_1$–$C_3$ thioalkyl, phenyl or furyl; $C_3$–$C_5$ alkenyl, halogen substituted $C_3$–$C_5$ alkenyl; phenyl substituted $C_3$–$C_5$ alkenyl; $C_3$–$C_5$ alkynyl, phenyl substituted $C_3$–$C_5$ alkynyl; hydroxy-substituted $C_3$–$C_5$ alkynyl or a halo, methyl or methoxyl substituted phenyl.

3. The compound of claim 2 wherein M is hydrogen.

4. The compound of claim 2 wherein M is an ion of sodium, potassium, lithium, rubidium, beryllium, magnesium, calcium, strontium or barium.

5. The compound of claim 2 wherein M is an ion of sodium or calcium.

6. The compound of claim 2 wherein M is an organic ammonium cation formed from an amine selected from the group consisting of methylamine, ethylamine, n-propylamine, isopropylamine, n-butylamine, isobutylamine, sec-butylamine, n-amylamine, iso-amylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, diheptylamine, dioctylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, tauroamine, cyclopentylamine, cyclohexylamine, dicyclohexylamine, piperidine, morpholine, pyrrolidine, tetramethylammonium hydroxide, tetraethylammonium hydroxide, trimethylbenzylammonium hydroxide and trimethyl beta-hydroxyethyl ammonium hydroxide.

7. The compound of claim 2 wherein M is a $C_1$–$C_{12}$ alkyl or $C_1$–$C_{12}$ alkyl substituted by $C_1$–$C_3$ alkoxy.

8. The compound of claim 2 wherein M is $H_3NR$ where R is

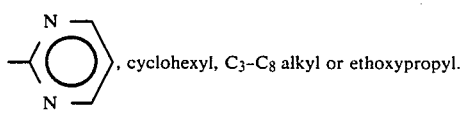, cyclohexyl, $C_3$–$C_8$ alkyl or ethoxypropyl.

9. An herbicidal composition containing an herbicidally effective amount of an imidazoline compound represented by the formula:

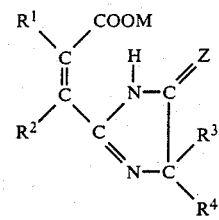

or

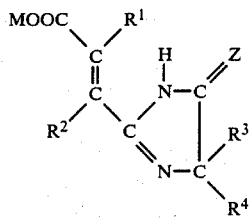

wherein $R^1$ and $R^2$ each represent a hydrogen atom, a loweralkyl group, a $C_3$–$C_6$ cycloalkyl group or a phenyl group, $R^3$ and $R^4$ each represent a lower alkyl group, a $C_3$–$C_6$ cycloalkyl group or a $C_3$–$C_6$ cycloalkyl group in which $R^3$ and $R^4$ are bonded together, Z represents an oxygen atom or a sulfur atom, and M represents a hydrogen atom, a base residue or an ester residue in an agriculturally acceptable carrier, and wherein said base residue is an alkali metal, an alkaline earth metal or an organic ammonium cation;

said ester residue is $C_1$–$C_{12}$ alkyl; $C_1$–$C_{12}$ alkyl substituted with $C_1$–$C_3$ alkoxy, $C_3$–$C_6$ cycloalkyl, halogen, $C_1$–$C_3$ thioalkyl, phenyl or furyl; $C_3$–$C_5$ alkenyl; a halogen-substituted $C_3$–$C_5$ alkenyl; phenyl-substituted $C_3$–$C_5$ alkenyl; $C_3$–$C_5$ alkynyl; phenyl-substituted $C_3$–$C_5$ alkynyl; a hydroxyl substituted $C_3$–$C_5$ alkynyl; and a substituted phenyl group having substituents selected from the group consisting of halogen, methyl and methoxy.

10. The herbicidal composition of claim 9 comprising 10 to 80% by weight of said imidazoline compound.

11. The herbicidal composition of claim 9 comprising 1 to 15% by weight of said imidazoline compound and further comprising 80 to 97% by weight of a solid carrier and 2 to 5% by weight of a surface active agent in said agriculturally acceptable carrier.

12. A plant growth regulating composition containing a plant growth regulating effective amount of imidazoline derivative represented by the general formula:

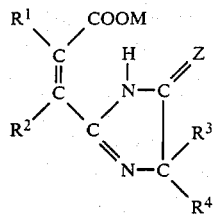

or

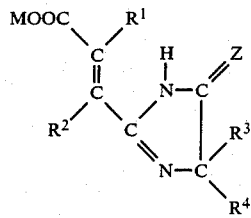

wherein $R^1$ and $R^2$ each represent a hydrogen atom, a lower alkyl group, a $C_3$–$C_6$ cycloalkyl group or a phenyl group, $R^3$ and $R^4$ each represent a lower alkyl group, a $C_3$–$C_6$ cycloalkyl group or a $C_3$–$C_6$ cycloalkyl group in which $R^3$ and $R^4$ are bonded together, Z represents an oxygen atom or a sulfur atom, and M represents a hydrogen atom, a base residue or an ester residue in an agriculturally acceptable carrier, and wherein said base residue is an alkali metal, an alkaline earth metal or an organic ammonium cation;

said ester residue is $C_1$–$C_{12}$ alkyl; $C_1$–$C_{12}$ alkyl substituted with $C_1$–$C_3$ alkoxy, $C_3$–$C_6$ cycloalkyl, halogen, $C_1$–$C_3$ thioalkyl, phenyl or furyl; $C_3$–$C_5$ alkenyl; a halogen-substituted $C_3$–$C_5$ alkenyl; phenyl-substituted $C_3$–$C_5$ alkenyl; $C_3$–$C_5$ alkynyl; phenyl-substituted $C_3$–$C_5$ alkynyl; a hydroxyl substituted $C_3$–$C_5$ alkynyl; and a substituted phenyl group having substituents selected from the group consisting of halogen, methyl and methoxy.

13. The plant growth regulating composition of claim 12 comprising 10 to 80% by weight of said imidazoline compound.

14. The plant growth regulating composition of claim 12 comprising 1 to 15% by weight of said imidazoline compound, and further comprising 80 to 97% by weight of a solid carrier and 2 to 5% by weight of a surface active agent in said agriculturally acceptable carrier.

15. A method of controlling weeds in a field of crops comprising applying an herbicidally effective amount of the compound of claim 1.

16. A method of plant growth regulating comprising applying to the plant, a plant growth regulating amount of the compound of claim 1.

* * * * *

Notice of Adverse Decision in Interference

In Interference No. 102,173, involving Patent No. 4,726,835, M. Uemura, M. Sakamoto and N. Kikkawa, HERBICIDAL AND PLANT GROWTH REGULATING IMIDAZOLINE DERIVATIVES, final judgment adverse to the patentees was rendered Sept. 21, 1989, as to claims 1-16.

[*Official Gazette November 21, 1989* ]